US009138385B2

(12) United States Patent
Dahl et al.

(10) Patent No.: US 9,138,385 B2
(45) Date of Patent: Sep. 22, 2015

(54) MICROEMULSION OF POLYSILOXANES CONTAINING QUATERNARY AMMONIUM GROUPS, PRODUCTION AND USE THEREOF

(75) Inventors: Verena Dahl, Köln (DE); Sascha Herrwerth, Essen (DE); Christian Hartung, Essen (DE); Joachim Venzmer, Essen (DE); Dirk Kuppert, Aschaffenburg (DE); Berend-Jan De Gans, Müllheim an der Ruhr (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 14/127,820

(22) PCT Filed: Mar. 19, 2012

(86) PCT No.: PCT/EP2012/054785
§ 371 (c)(1),
(2), (4) Date: Dec. 19, 2013

(87) PCT Pub. No.: WO2013/000592
PCT Pub. Date: Jan. 3, 2013

(65) Prior Publication Data
US 2014/0134125 A1 May 15, 2014

(30) Foreign Application Priority Data
Jun. 30, 2011 (DE) .......................... 10 2011 078 382

(51) Int. Cl.
*A61Q 5/12* (2006.01)
*A61K 8/06* (2006.01)
*A61K 8/898* (2006.01)
*B01F 17/54* (2006.01)
*C11D 3/37* (2006.01)
*C11D 17/00* (2006.01)
*A61Q 5/02* (2006.01)
*A61Q 19/00* (2006.01)
*A61Q 19/10* (2006.01)
*C09D 7/12* (2006.01)
*D06M 15/643* (2006.01)
*B01F 17/00* (2006.01)
*C11D 3/16* (2006.01)
*A61Q 5/00* (2006.01)
*A61Q 5/06* (2006.01)

(52) U.S. Cl.
CPC ................ *A61K 8/068* (2013.01); *A61K 8/898* (2013.01); *A61Q 5/02* (2013.01); *A61Q 5/12* (2013.01); *A61Q 19/00* (2013.01); *A61Q 19/10* (2013.01); *B01F 17/0071* (2013.01); *C09D 7/125* (2013.01); *C11D 3/3742* (2013.01); *C11D 17/0021* (2013.01); *A61Q 5/00* (2013.01); *A61Q 5/06* (2013.01); *B01F 17/0042* (2013.01); *C11D 3/162* (2013.01); *D06M 15/643* (2013.01); *D06M 15/6436* (2013.01)

(58) Field of Classification Search
CPC ........... A61Q 5/02; A61Q 9/10; A61K 8/068; B01F 17/0071; B01F 17/0042; C11D 17/0071; C11D 17/0042; D06M 15/643; D06M 15/6436
USPC ...................................... 424/70.122
See application file for complete search history.

(56) References Cited

U.S. PATENT DOCUMENTS

| | | | |
|---|---|---|---|
| 4,426,299 A | 1/1984 | Verbruggen | |
| 4,620,878 A | 11/1986 | Gee | |
| 4,749,732 A | 6/1988 | Kohl et al. | |
| 4,806,255 A | 2/1989 | Konig et al. | |
| 4,855,072 A | 8/1989 | Trinh et al. | |
| 6,153,569 A | 11/2000 | Halloran | |
| 6,607,717 B1 | 8/2003 | Johnson et al. | |
| 7,361,777 B2 | 4/2008 | Herrwerth et al. | |
| 7,442,666 B2 | 10/2008 | Herrwerth et al. | |
| 7,598,334 B2 | 10/2009 | Ferenz et al. | |
| 7,605,284 B2 | 10/2009 | Brueckner et al. | |
| 7,727,599 B2 | 6/2010 | Doehler et al. | |
| 7,759,402 B2 | 7/2010 | Venzmer et al. | |
| 7,834,122 B2 | 11/2010 | Ferenz et al. | |
| 7,964,694 B2 | 6/2011 | Ferenz et al. | |
| 8,076,440 B2 | 12/2011 | Kuppert et al. | |
| 8,084,633 B2 | 12/2011 | Herrwerth et al. | |
| 8,466,248 B2 | 6/2013 | Meyer et al. | |
| 2004/0102570 A1 | 5/2004 | Johnson et al. | |
| 2004/0258651 A1 | 12/2004 | Pascaly et al. | |
| 2007/0197678 A1 | 8/2007 | Cavaleiro et al. | |
| 2007/0212326 A1 | 9/2007 | Ochs et al. | |

(Continued)

FOREIGN PATENT DOCUMENTS

CN 1791376 A 6/2006
CN 1993403 A 7/2007

(Continued)

OTHER PUBLICATIONS

International Search Report dated Jul. 11, 2012 issued in PCT/EP2012/054785.
English Abstract of corresponding EP 0375923 A1 dated Jul. 4, 1990.
Chinese Office Action and Search Report mailed Oct. 10, 2014, issued in Application No. 201280032468.8 (in Chinese and in English).
Schrader, K. et al., "Grundlagen and Rezepturen der Kosnrietika" ["Principles and Formulations of Cosmetics"], 1989, 2nd edition, p. 329 to 341, Hüthig Buch Verlag Heidelberg.
Chinese Office Action dated May 7, 2015, received in a corresponding foreign application and English-language translation thereof.

*Primary Examiner* — Margaret Moore
(74) *Attorney, Agent, or Firm* — Scully, Scott, Murphy & Presser, P.C.

(57) ABSTRACT

The invention relates to microemulsions which comprise, as oil phase, a polysiloxane containing at least one quaternary ammonium group, methods for production thereof and also to the use of such microemulsions.

10 Claims, 2 Drawing Sheets

(56) References Cited

U.S. PATENT DOCUMENTS

| | | |
|---|---|---|
| 2008/0251751 A1 | 10/2008 | Bruckner et al. |
| 2008/0305065 A1 | 12/2008 | Ferenz et al. |
| 2009/0007483 A1 | 1/2009 | Hansel et al. |
| 2009/0324530 A1 | 12/2009 | Yang et al. |
| 2010/0034765 A1 | 2/2010 | Herrwerth et al. |
| 2010/0184634 A1 | 7/2010 | Henault et al. |
| 2010/0266651 A1 | 10/2010 | Czech et al. |
| 2011/0070175 A1 | 3/2011 | Herrwerth et al. |
| 2011/0144269 A1 | 6/2011 | Kuppert et al. |
| 2011/0230619 A1 | 9/2011 | Kuppert et al. |
| 2012/0027704 A1 | 2/2012 | Henning et al. |
| 2012/0097883 A1 | 4/2012 | Henning et al. |
| 2012/0168664 A1* | 7/2012 | Maurer et al. ............... 252/8.57 |
| 2012/0294819 A1 | 11/2012 | Herrwerth et al. |
| 2012/0329955 A1 | 12/2012 | Kuppert et al. |
| 2013/0035452 A1 | 2/2013 | Kuppert et al. |
| 2013/0040875 A1 | 2/2013 | Henning et al. |

FOREIGN PATENT DOCUMENTS

| | | |
|---|---|---|
| CN | 101117385 A | 2/2008 |
| CN | 101314640 A | 12/2008 |
| CN | 101815744 | 8/2010 |
| DE | 3839937 A1 | 5/1990 |
| DE | 19751151 A1 | 5/1999 |
| DE | 10327871 A1 | 1/2005 |
| EP | 0459500 A2 | 12/1991 |
| EP | 1426398 A1 | 6/2004 |
| EP | 1887024 A1 | 2/2008 |
| EP | 2273966 A0 | 1/2011 |
| WO | WO9201776 | 2/1992 |
| WO | WO9524460 | 9/1995 |
| WO | WO9731997 | 9/1997 |
| WO | WO9731998 | 9/1997 |
| WO | WO 03106575 A1 | 12/2003 |
| WO | WO2004103326 | 12/2004 |
| WO | 2006/013017 A1 | 2/2006 |
| WO | WO2007115872 A1 | 10/2007 |
| WO | WO2007125005 A1 | 11/2007 |
| WO | WO2009138306 A1 | 11/2009 |
| WO | 2011/032797 * | 3/2011 |
| WO | WO 2011042409 A2 | 4/2011 |
| WO | WO2011088937 A1 | 7/2011 |

\* cited by examiner

MICROEMULSION OF POLYSILOXANES CONTAINING QUATERNARY AMMONIUM GROUPS, PRODUCTION AND USE THEREOF

FIELD OF THE INVENTION

The invention relates to microemulsions which have, as oil phase, a polysiloxane containing at least one quaternary ammonium group, processes for their preparation, and the use of such microemulsions.

PRIOR ART

Polysiloxanes with quaternary groups and their use as additives for hair care or textile softeners are known from the patent literature.

EP 1887024 with the filing date 4 Jul. 2007 describes terminally cationic polysiloxanes with a so-called T structure and their use as conditioners in cosmetic formulations. These cationic polysiloxanes exhibit a pronounced conditioning and shine-generating effect. However, the potentially more effective higher molecular weight cationic polysiloxanes with this T structure have the problem that they are of extremely high viscosity and thus cannot be handled or incorporated into cosmetic formulations. The same statement can apply to the multimeric polysiloxanes having T structures disclosed in PCT/EP2010/070071 with filing date 17 Dec. 2010.

One option of incorporating polysiloxanes into cosmetic formulations is the presentation form of the polyorganosiloxanes in the form of emulsions or microemulsions. Microemulsions are thermodynamically stable mixtures of water (aqueous phase), oil (water-immiscible phase) and surfactant (solubilizer). Microemulsions in which the oil phases are substantially formed by polysiloxanes are known.

U.S. Pat. No. 4,620,878 describes the general preparation of emulsions and microemulsions which comprise linear aminofunctional polyorganosiloxanes. First of all, a concentrate consisting of surfactant, polyorganosiloxane and small amounts of water is prepared, which is then rapidly dispersed in the remaining water required for forming the microemulsion.

EP 0459500 describes how polysiloxane-containing microemulsions are prepared by emulsion polymerization.

U.S. Pat. No. 6,607,717 describes the preparation and use of emulsions and other formulations with comb-like, quaternary polyorganosiloxanes using nonionic ethoxylated emulsifiers.

U.S. Pat. No. 4,749,732 describes the use of aminoalkyl-substituted polyorganosiloxanes and their presentation as emulsion or microemulsion for clear hair care applications.

U.S. Pat. No. 6,153,569 describes the use of microemulsions with aminofunctional polyorganosiloxanes in order to obtain clear shampoo formulations.

Softener compositions, which are used in the rinse cycle after the cleaning or washing of fabrics and/or textiles, are known. Furthermore, it is known that softener compositions can comprise one or more silicones or organically modified siloxanes which reduce creasing of fabric after the rinse cycle and drying, facilitate ironing, and bring about increased softness or improved rewettability. This is disclosed for example in WO 9524460, GB 1596792, U.S. Pat. No. 4,426,299, U.S. Pat. No. 4,806,255, and U.S. Pat. No. 4,855,072.

The use of microemulsions for incorporating silicones into softener formulations is described for example in WO 92/01776.

The use of macroemulsions for incorporating silicones into softener formulations is described e.g. in WO A 97/31997 and WO A 97/31998.

Aqueous coatings which comprise polyurethane dispersions as binders are likewise known. Such dispersions are referred to as single-component or 1C systems and are used for the coating of substrates of every type, preferably textile, metal, leather, plastic, paper, cardboard and wood. These are polymer chains which are bonded by urethane or urea bonds and likewise contain acid groups, such as for example carboxylates or sulphonates, or alkaline groups, such as for example amines. By means of subsequent neutralization it is possible to convert such polyurethanes to stable aqueous dispersions. Such 1C systems are often post-crosslinked by adding a water-soluble crosslinker, such as for example water-soluble melamine resins. Moreover, additional groups can be incorporated in the molecule which bring about crosslinking after drying. A detailed description of polyurethane dispersions, their chemotechnical principles and fields of application can be found for example in the book "Polyurethane für Lacke and Beschichtungen [Polyurethanes for coatings]" (Manfred Bock, Vincentz Verlag, Hannover 1999).

It is known that coatings based on such polyurethane dispersions can contain one or more silicones or organically modified siloxanes which reduce the soiling tendency and the sliding friction, which eliminate stick-slip, hydrophobize the surface and improve the haptics. This is disclosed for example in the documents DE 3839937 and WO 03/106575.

A disadvantage of all of the microemulsions described in the prior art is that all of the nonionic surfactants referred to as being suitable are without exception alkoxylated compounds.

Moreover, all of the microemulsions described in the prior art contain exclusively siloxanes which have no pronounced silicone character and do not have good efficacy as conditioning agents for e.g. hair or textiles, or have proportionately a low affinity towards certain surfaces.

It was an object of the present invention to find a way of making polysiloxanes, in particular those which have a high viscosity at room temperature, handleable for applications.

DESCRIPTION OF THE INVENTION

Figure 1:
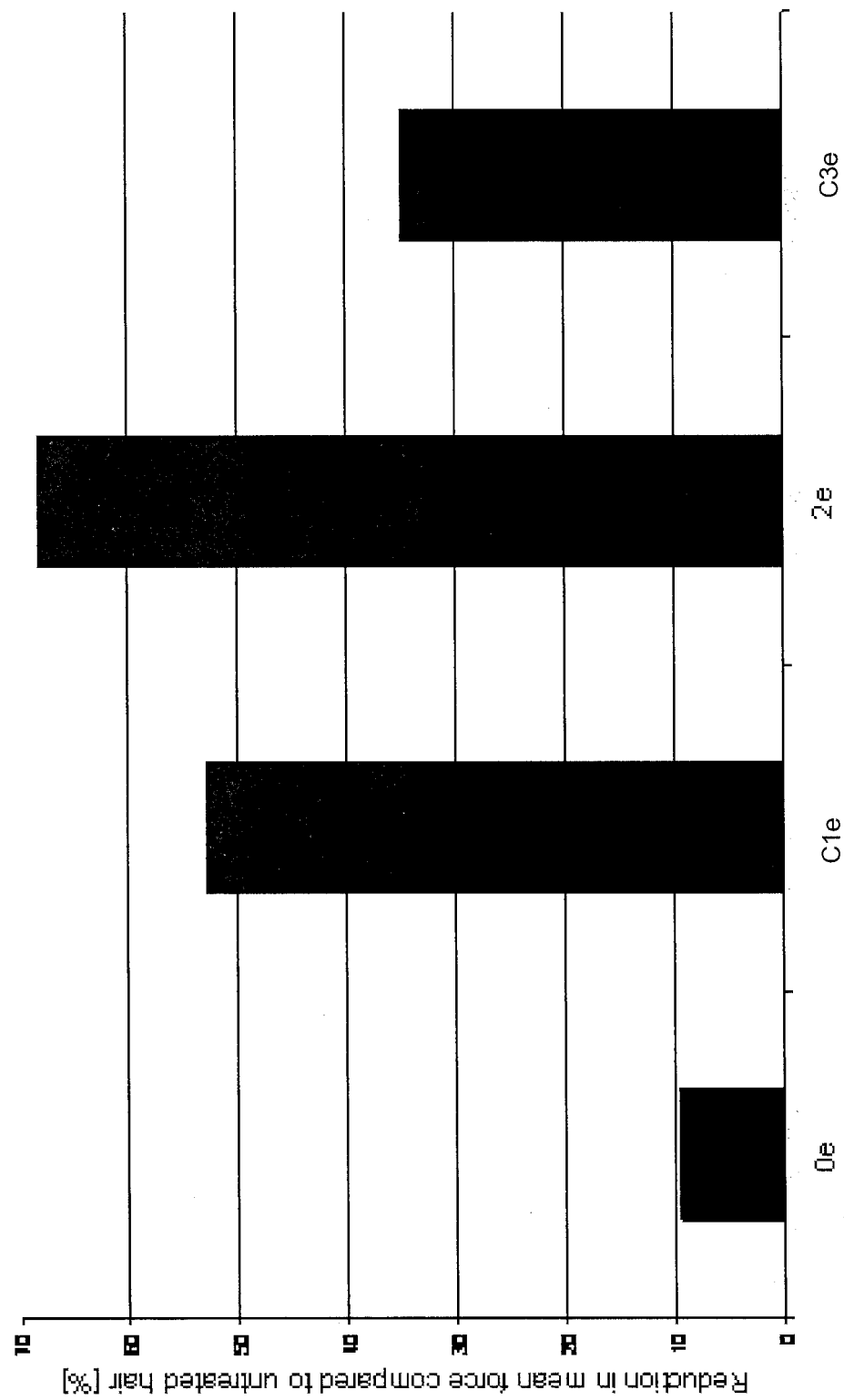
FIG. 1 is part of the examples and shows the lowering of the friction as a result of using conditioners.

Surprisingly, it has been found that the microemulsions described below are able to achieve the object set by the invention.

The present invention therefore provides microemulsions which comprise, as component substantially forming the oil phase, certain quaternary polysiloxanes with (multi-) T structure.

The invention further provides a process for the preparation of the microemulsions according to the invention, the use of the microemulsions according to the invention for producing formulations, and the formulations comprising the microemulsions according to the invention.

One advantage of the microemulsions according to the invention is that highly viscous quaternary polysiloxanes with a (multi-) T structure can be converted to a low viscosity state without losing their functionality and/or activity, but, on the contrary, even increasing the activity in applications.

Another advantage of the present invention is that the quaternary polysiloxanes with a (multi-) T structure achieve a better performance in formulations. The microemulsions of the present invention enhance the conditioning properties of the quaternary polysiloxanes present having a (multi-) T structure such as combability, softness, volume, shapeability, manageability, the ability of undamaged and damaged hair to be detangled and shine effect, and also the care and cleaning effect of formulations for the home and industry. Furthermore, by using microemulsions, an improved softness feel is produced for textiles, in particular for textiles made of cotton materials, than when using e.g. macroemulsions.

Another advantage of the present invention is that quaternary polysiloxanes with a (multi-) T structure can be incorporated into cosmetic formulations which, in pure form or diluted in suitable solvents, cannot be incorporated into cosmetic formulations on account of the high viscosity or the lack of compatibility.

Another advantage is that the microemulsions according to the invention for cosmetic applications can be prepared essentially free from alkoxylated constituents.

Yet another advantage of the microemulsions according to the invention comprising silicone quats with a (multi-) T structure is that they have a particularly good conditioning effect in cosmetic, dermatological and pharmaceutical formulations.

It is a further advantage of the invention that otherwise water-insoluble quaternary polysiloxanes with a (multi-) T structure can be converted to a water-dilutable form.

The present invention provides a microemulsion comprising, as component substantially forming the oil phase, A) polysiloxane containing at least one quaternary ammonium group and of the general formula (I)

$$M_a M'_{a1} M''_{a2} M'''_{a3} D_b D'_{b1} D''_{b2} D'''_{b3} T_c T'_{c1} Q_d \quad \text{formula (I)},$$

where
$M=(R^1_3SiO_{1/2})$
$M'=(R^2R^1_2SiO_{1/2})$
$M''=(R^3R^1_2SiO_{1/2})$
$M'''=(R^4R^1_2SiO_{1/2})$
$D=(R^1_2SiO_{2/2})$
$D'=(R^2R^1SiO_{2/2})$
$D''=(R^3R^1SiO_{2/2})$
$D'''=(R^4R^1SiO_{2/2})$
$T=(R^5SiO_{3/2})$
$T'=(R^2SiO_{3/2})$
$Q=(SiO_{4/2})$
a=0 to 32; preferably 0 to 22, in particular 0 to 12;
a1=0 to 10, preferably 0 to 5, in particular 0;
a2=0 to 32; preferably 0 to 22, in particular 1 to 12;
a3=0 to 10; preferably 0 to 5, in particular 0;
with the proviso that
a+a1+a2+a3≥3, in particular 3 to 22, preferably >3, in particular 4 to 17;
b=1 to 600, preferably 10 to 500, in particular 20 to 400;
b1=0 to 10, preferably 0 to 5, in particular 0;
b2=0 to 80, preferably 0 to 50, in particular 0 to 10;
b3=0 to 20, preferably 0 to 10, in particular 0;
c=0 to 30, preferably 1 to 20, in particular 2 to 15;
c1=0 to 10, preferably 0 to 5, in particular 0;
d=0 to 15, preferably 1 to 12, in particular 2 to 10;
with the proviso that
a2+b2≥1, preferably 3, in particular >3 and
c+c1+d≥1, preferably 1 to 20, preferably >1, in particular 2 to 15, in particular ≥3;

$R^1$=independently of one another identical or different linear or branched, optionally aromatic hydrocarbon radicals having 1 to 30 carbon atoms, preferably methyl or phenyl, in particular methyl;

$R^2$=independently of one another identical or different alkoxy or acyloxy radicals, such as for example methoxy, ethoxy, n-propoxy or isopropoxy radicals, acetoxy, in particular ethoxy or isopropoxy radicals;

$R^3$=independently of one another identical or different organic radicals which carry quaternary ammonium functions;

$R^4$=independently of one another identical or different organic epoxy radicals;

$R^5$=independently of one another identical or different radicals $R^1$, $R^3$ or $R^4$, preferably $R^1$, in particular methyl, phenyl, dodecyl or hexadecyl.

In connection with the present invention, the term "component substantially forming the oil phase" is understood as meaning that the polysiloxane constitutes at least 50% by weight of the oil phase; the remaining fraction of the oil phase can consist for example of the component referred to below as component G.

The polysiloxanes described in the course of the invention can have different units multiple times; these may occur in these compounds in random distribution (random oligomer) or ordered (block oligomer). It is known to the person skilled in the art that the compounds in the form of a mixture are present with a distribution regulated essentially by laws of statistics. Details relating to the number of units in such compounds are to be understood as meaning average value, averaged over all of the corresponding compounds. All of the percentages given (%), unless stated otherwise, are percentages by mass. All of the conditions such as, for example, pressure and temperature, unless stated otherwise, are standard conditions.

Polysiloxanes present in the microemulsions according to the invention preferably comprise, as epoxy radicals $R^4$, preferably identical or different radicals selected from the group

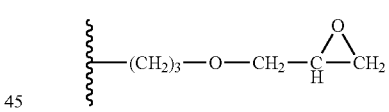

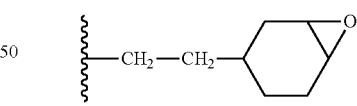

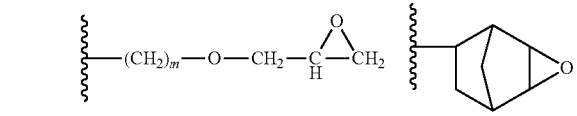

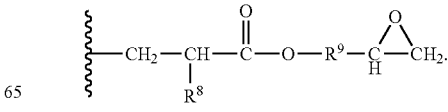

Suitable radicals $R^3$ are for example groups with the structure —$R^6$—$R^7$, in which $R^6$ are preferably identical or different divalent radicals, selected from the group

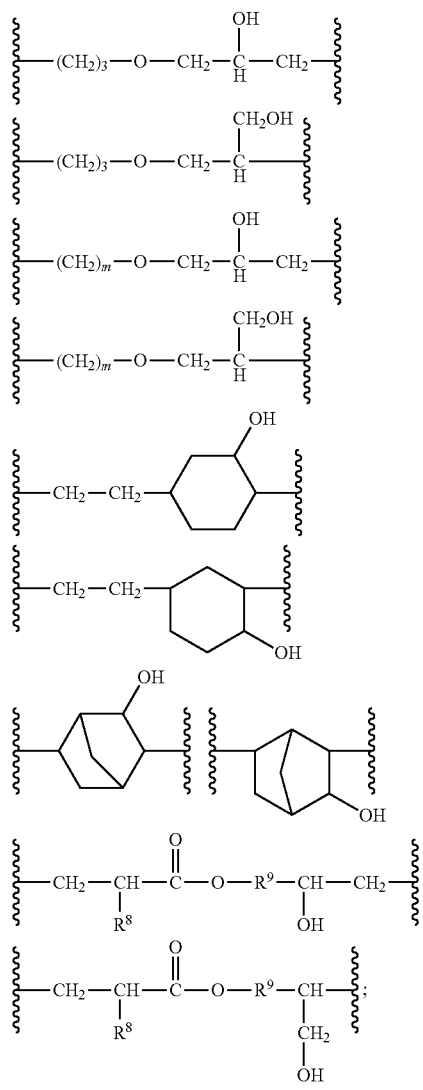

$R^6$ is particularly preferably:

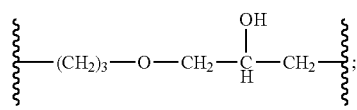

$R^7$ is selected from the group consisting of

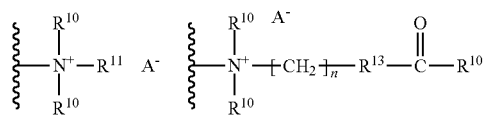

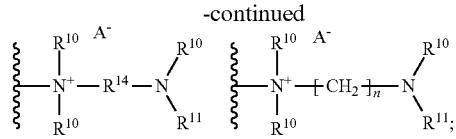

$R^8$ are identical or different radicals from the group hydrogen or alkyl having 1 to 6 carbon atoms, preferably methyl;

$R^9$ are identical or different divalent hydrocarbon radicals which optionally contain ether functions, preferably methylene;

$R^{10}$, $R^{11}$, $R^{12}$ are in each case independently of one another hydrogen or alkyl radicals having 1 to 30 carbon atoms or radicals of the formula

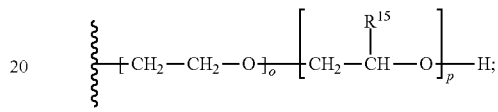

$R^{13}$ are identical or different radicals from the group —O—; —$NR^{16}$—;

$R^{14}$ are identical or different optionally branched divalent hydrocarbon radicals, preferably ethylene or propylene;

$R^{15}$ are identical or different alkyl, aryl or alkaryl radicals having 1 to 30 carbon atoms which optionally contain ether functions, preferably methyl, ethyl or phenyl, in particular methyl;

$R^{16}$ are identical or different radicals from the group hydrogen or alkyl having 1 to 6 carbon atoms;

m=2 to 18;

n=2 to 18, preferably 3;

o=0 to 30, preferably 0 to 10, in particular 1 to 3;

p=0 to 30, preferably 0 to 10;

$A^-$ are identical or different counterions to the positive charges on the quaternized nitrogen groups, selected from inorganic or organic anions of the acids HA, and derivatives thereof.

In a further preferred embodiment of the present invention, the counterion A to the positive charges on the quaternized nitrogen groups consists of the anion of a physiologically compatible acid HA, which is particularly preferably selected from acetic acid, L-hydroxycarboxylic acids, in particular lactic acid, or aromatic carboxylic acids. Further preferred counterions originate from customary quaternizing agents. These are in particular ethyl sulphate, methyl sulphate, toluenesulphonate, chloride and bromide.

It is one embodiment of the present invention, the microemulsions according to the invention comprise at least one polysiloxane which has a simple T structure with terminal modification, thus is characterized in that the microemulsion comprises a polysiloxane where c=1 and c+c1+d=1 (consequently c1=d=0) and a2≥1 where a2+a3=3 and a=a1=b1=b2=b3=0.

The polysiloxanes present in the microemulsions according to the invention can be prepared by processes as described in the documents EP 1887024 and PCT/EP2010/070071 specified above, where preferably the process specified in EP 1887024 is used for producing the polysiloxanes with a simple T structure. As regards the preparation process, reference is made explicitly to the disclosure in these documents, which replaces the description in the present document.

In the microemulsions of the present invention, polysiloxanes with an average molecular weight of greater than 4000 g/mol, preferably of greater than 7000 g/mol, in particular of greater than 10 000 g/mol are advantageously used, the average molecular weight being determined by means of $^{29}$Si NMR.

Microemulsions preferred according to the invention have a domain size of the disperse phase of less than 1000 nm, in particular less than 500 nm, the determination of the domain size being carried out with the help of scattering methods known to the person skilled in the art, as described for example in P. Lindner and Th. Zemb, "Neutrons, X-Rays and Light: Scattering Methods Applied to Soft Condensed Matter", Elsevier Science & Technology, November 2002 or O. Glatter and O. Kratky, "Small-angle X-ray Scattering" Academic Press Inc, December 1982.

In the microemulsions of the present invention, polysiloxanes with a viscosity of >1 Pas, in particular of 10 Pas to 100 000 Pas (measured using plate-plate geometry of a rheometer at T=25° C., gap width of 1 mm at a shear rate of 1 $s^{-1}$) are advantageously used.

Microemulsions preferred according to the invention are characterized in that they additionally comprise at least one of the components B) at least one nonionic surfactant;

C) a cosurfactant selected from the group comprising, preferably consisting of anionic, cationic and amphoteric surfactants; and D) water.

Microemulsions preferred according to the invention are characterized in that they additionally comprise at least one of the components B) and C) or B) and D) or C) and D) or B) and C) and D).

Preferred nonionic surfactants are selected from the group comprising, preferably consisting of, addition products of ethylene oxide and/or propylene oxide onto linear fatty alcohols, fatty acids, fatty acid amides, fatty amines and onto alkylphenols, glycerol mono- and diesters and sorbitan mono- and diesters of saturated and unsaturated fatty acids and ethylene oxide addition products thereof, alkyl mono- and oligoglycosides and ethylene oxide addition products thereof, addition products of ethylene oxide onto castor oil and/or hydrogenated castor oil, partial esters based on linear, branched, unsaturated or saturated fatty acids, ricinoleic acid, 12-hydroxystearic acid, glycerol, polyglycerol, pentaerythritol, dipentaerythritol and sugar alcohols (e.g. sorbitol), alkyl glucosides (e.g. methyl glucoside, butyl glucoside, lauryl glucoside), and polyglucosides (e.g. cellulose), mono-, di- and trialkyl phosphates, and mono-, di- and/or tri-PEG alkyl phosphates and salts thereof, citric acid esters such as e.g. glyceryl stearate citrate, glyceryl oleate citrate and dilauryl citrate, and glyceryl caprylate, polyglycerylcaprylate, polyglycerylcaprate, further alkoxylated triglycerides, mixed ethers and mixed formals, optionally partially oxidized alkyl oligoglycosides or alkenyl oligoglycosides or glucuronic acid derivatives, fatty acid N-alkylglucamides, protein hydrolysates (in particular wheat-based vegetable products), polyol fatty acid esters, sugar esters, polysorbates and amine oxides and mixtures of these surfactants.

If the nonionic surfactants contain polyglycol ether chains, these can have a conventional homologue distribution, but preferably have a narrowed homologue distribution.

In connection with the present invention, the term "fatty acids" is to be understood in particular as meaning formic acid, acetic acid, propionic acid, butyric acid, valeric acid, caproic acid, oenanthic acid, carprylic acid, perlargonic acid, capric acid, lauric acid, myristic acid, pentadecanoic acid, palmitic acid, margaric acid, stearic acid, nonadecanoic acid, arachic acid, behenic acid, lignoceric acid, cerotinic acid, montanic acid, mellissic acid, undecylenic acid, myristoleic acid, palmitoleic acid, petroselic acid, oleic acid, elaidic acid, vaccenic acid, gadoleic acid, icosenoic acid, cetoleic acid, erucic acid, nervonic acid, linolic acid, alpha-linolenic acid, gamma-linolenic acid, calendulic acid, punicic acid, alpha-elaeostearic acid, beta-elaeostearic acid, arachidonic acid, timnodonic acid, clupanodonic acid, cervonic acid, vernolic acid, ricinoleic acid, particular preference being given to those with chain length of 6 to 22, in particular 8 to 18 carbon atoms; the same applies to the carbon backbone for the term "fatty alcohols" used in connection with the invention.

Preferred anionic surfactants are those having a carbon/late, sulphate, sulphonate or phosphate group and a lipophilic radical.

Typical examples of anionic surfactants are soaps, alkylbenzenesulphonates, alkanesulphonates, olefinsulphonates, alkyl ether sulphonates, glycerol ether sulphonates, alpha-methyl ester sulphonates, sulpho fatty acids, alkylsulphates, alkyl ether sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulphosuccinates, mono- and dialkyl sulphosuccinamates, suiphotriglycerides, amide soaps, alkyl ether carboxylates, ether carboxylic acids and salts thereof, acyl sarcosinates, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulphates, protein fatty acid condensates (in particular wheat-based vegetable products) and alkyl (ether) phosphates and mixtures of these surfactants.

If the anionic surfactants contain polyglycol ether-chains, these can have a conventional homologue distribution, but preferably have a narrowed homologue distribution.

Cationic surfactants which can be used are in particular quaternary ammonium compounds, in particular those provided with at least one linear and/or branched, saturated or unsaturated alkyl chain, such as for example alkyltrimethylammonium halides such as e.g. cetyltrimethylamnnonium chloride or bromide or behenyltrimethylammonium chloride, but also dialkyldimethylammonium halides such as e.g. distearyldimethylammonium chloride. Furthermore, monoalkylamidoquats such as e.g. palmitamidopropyltrimethylammonium chloride or corresponding dialkylamidoquats can be used as cationic surfactants.

Furthermore, cationic surfactants which can be used are quaternary ester compounds, which may be quaternized fatty acid esters based on mono-, di or triethanolamine. Cationic surfactants can also be alkylguanidinium salts.

Typical examples of amphoteric surfactants are amphoacetates, amphopropionates, alkylbetaines, alkylamidobetaines, aminopropionates, aminoglycinates, imidazoliniumbetaines and sulphobetaines such as e.g. the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and also cocoacylaminoethylhydroxyethyl carboxymethylglycinate. A preferred zwitterionic surfactant is the fatty acid amide derivative known under the INCI name Cocamidopropyl Betaine.

For cosmetic or topical applications in particular, preference is given to microemulsions which are essentially free from alkoxylated compounds. In connection with the present invention, the term "essentially free from alkoxylated compounds" is to be understood as meaning that the microemulsion has no noteworthy amounts of alkoxylated compounds which exert a surface-active effect. In particular, this is to be understood as meaning that alkoxylated compounds are present in amounts of less than 1% by weight, preferably of less than 0.1% by weight, particularly preferably of less than 0.01% by weight, based on the total microemulsion, in particular no detectable amounts are present. In such microemulsions essentially free from alkoxylated compounds, in particular nonionic surfactants of component B) selected from the group consisting of glycerol mono- and diesters and sorbitan mono- and diesters of saturated and unsaturated fatty acids, alkyl mono- and oligoglycosides, partial esters based on linear, branched, unsaturated or saturated fatty acids, ricinoleic acid and 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside), and polyglucosides (e.g. cellulose), mono-, di- and trialkyl phosphates and salts thereof, citric acid esters such as e.g. glyceryl stearate citrate, glyceryl oleate citrate and dilauryl citrate, and glyceryl caprylate, polyglycerylcaprylate, polyglycerylcaprate and mixtures of these surfactants, are present.

Since the presence of a solvent can simplify the preparation of the emulsion in the preparation process of the microemulsions, preferred microemulsions of the present invention are characterized in that additionally a solvent E) is present selected from the group comprising, preferably consisting of, hydrotropes, for example from the group of aliphatic alcohols, such as ethanol, propanol or 1,3-propanediol, cyclic carbonates such as ethylene carbonate, propylene carbonate, glycerol carbonate, esters of mono- or polycarboxylic acids such as ethyl acetate, ethyl lactate, glycerol, isopropyl alcohol, dipropylene glycol, glycol ether (available for example under the name DOWANOL® from Dow Chemicals) or polyols. Polyols which are suitable here can have 2 to 15 carbon atoms and at least two hydroxyl groups. Typical examples are: glycerol, alkylene glycols, such as, for example, ethylene glycol, diethylene glycol, propylene glycol, butylene glycol, pentylene glycol, hexylene glycol, 1,2-propanediol, 1,2-butanediol, 1,2-pentanediol, 1,2-hexanediol, and polyethylene glycol or polypropylene glycol, polyhydroxycarboxylic acids, butyl diglycol and mixtures of these solvents.

In order to microbiologically stabilize the microemulsions according to the invention, it is advantageous if they contain a component F), preservatives. These may be for example mixtures of one or more alkylparaben esters with phenoxyethanol alone. The alkylparaben esters may be methylparaben, ethylparaben, propylparaben and/or butylparaben. Instead of phenoxyethanol it is also possible to use other alcohols, such as, for example, benzyl alcohol or ethanol. Moreover, it is also possible to use other preservatives, alone or in a mixture, such as for example phenoxyethanol, sorbic or benzoic acid, salicylic acid, 2-bromo-2-nitropropane-1,3-diol, chloroacetamide, diazolidinylurea, DMDM hydantoin, iodopropynyl butylcarbamate, sodium hydroxymethylglycinates, methylisothiazoline, chloromethyl-isothiazoline, ethylhexylglycerol or caprylyl glycol.

The oil phase of the microemulsion according to the invention can additionally a component G), an oil or oil mixture selected from the group comprising, preferably consisting of, propylene glycol monocaprylates, mono- or diesters of linear and/or branched mono- and/or dicarboxylic acids having 2 to 44 carbon atoms with linear and/or branched saturated or unsaturated alcohols having 1 to 22 carbon atoms; as well as esterification products of aliphatic, difunctional alcohols having 2 to 36 carbon atoms with monofunctional aliphatic carboxylic acids having 1 to 22 carbon atoms, long-chain arylic acid esters of linear or branched, saturated or unsaturated alcohols having 1 to 22 carbon atoms, or else isostearyl benzoate or octyldodecyl benzoate, monoesters (such as e.g. the methyl esters and isopropyl esters of fatty acids having 12 to 22 carbon atoms, such as e.g. methyl laurate, methyl stearate, methyl oleate, methyl erucate, isopropyl palmitate, isopropyl myristate, isopropyl stearate, isopropyl oleate, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate), as well as esters which are obtainable from technical-grade aliphatic alcohol cuts and technical-grade, aliphatic carboxylic acid mixtures; as well as naturally occurring monoester or wax ester mixtures, as are present e.g. in jojoba oil or in sperm oil. Suitable dicarboxylic acid esters are e.g. di-n-butyl adipate, di-n-butyl sebacate, di(2-ethylhexyl) adipate, di(2-hexyldecyl) succinate, diisotridecyl azelate. Suitable diol esters are e.g. ethylene glycol dioleate, ethylene glycol diisotridecanoate, propylene glycol di(2-ethylhexanoate), butanediol diisostearate, butanediol dicaprylate/caprate and neopentyl glycol dicaprylate. Further fatty acid esters which can be used are e.g. C12-15 alkylbenzoate, dicaprylylcarbonate, diethylhexylcarbonate. Longer-chain triglycerides, i.e. triple esters of glycerol with three acid molecules, of which at least one is longer-chain, can likewise be used as oil component; furthermore hydrocarbons, in particular also liquid paraffins and isoparaffins such as paraffin oil, isohexadecane, polydecene, liquid petroleum jelly, Paraffinum perliquidum, squalane, ceresin; and also linear or branched fatty alcohols such as oleyl alcohol or octyldodecanol and fatty alcohol ethers such as dicaprylyl ether; silicone oils and waxes such as e.g. polydimethylsiloxanes, cyclomethylsiloxanes, and also aryl- or alkyl- or alkoxy-substituted polymethylsiloxanes or cyclomethylsiloxanes, Guerbet alcohols based on fatty alcohols having 6 to 18, preferably 8 to 10, carbon atoms, esters of linear C6-C22 fatty acids with linear C6-C22 fatty alcohols, esters of branched C6-C13 carboxylic acids with linear C6-C22 fatty alcohols, esters of linear C6-C22 fatty acids with branched C8-C18 alcohols, in particular 2-ethylhexanol or isononanol, esters of branched C6-C13 carboxylic acids with branched alcohols, in particular 2-ethylhexanol or isononanol, esters of linear and/or branched fatty acids with polyhydric alcohols (such as e.g. propylene glycol, dimerdiol or trimertriol) and/or Guerbet alcohols, triglycerides based on C6-C10 fatty acids, liquid mono-/di-/triglyceride mixtures based on C6-C18 fatty acids, esters of C6-C22 fatty alcohols and/or Guerbet alcohols with aromatic carboxylic acids, in particular benzoic acid, vegetable oils, branched primary alcohols, substituted cyclohexanes, linear C6-C22 fatty alcohol carbonates, Guerbet carbonates, esters of benzoic acid with linear and/or branched C6-C22 alcohols (e.g. Finsolv™ TN), dialkyl ethers, ring-opening products of epoxidized fatty acid esters with polyols, silicone oils and/or aliphatic or naphthenic hydrocarbons comprise.

In this connection, the proviso that component G) constitutes at most 50% by weight of the total oil phase applies.

In microemulsions preferred according to the invention, component A) is present in an amount of from 10% by weight to 60% by weight, preferably in an amount of from 15% by weight to 50% by weight, particularly preferably in an amount of from 20% by weight to 45% by weight, the % by weights referring to the total microemulsion.

Particularly preferred microemulsion of the present invention are characterized in that

- component A) is present in an amount of from 10% by weight to 60% by weight, preferably in an amount of from 15% by weight to 50% by weight, particularly preferably in an amount of from 20% by weight to 45% by weight,
- component B) is present in an amount of from 3% by weight to 30% by weight, preferably in an amount of from 4% by weight to 20% by weight, particularly preferably in an amount of from 5% by weight to 15% by weight,
- component C) is present in an amount of from 0% by weight to 30% by weight, preferably in an amount of from 3% by weight to 25% by weight, particularly preferably in an amount of from 5% by weight to 20% by weight,
- component D) is present in an amount of from 10% by weight to 75% by weight, preferably in an amount of from 15% by weight to 65% by weight, particularly preferably in an amount of from 20% by weight to 55% by weight,
- component E) is present in an amount of from 0% by weight to 35% by weight, preferably in an amount of from 3% by weight to 30% by weight, particularly preferably in an amount of from 5% by weight to 25% by weight,
- component F) is present in an amount of from 0% by weight to 1% by weight, preferably in an amount of from 0.0001% by weight to 0.5% by weight, and
- component G) is present in an amount of from 0% by weight to 50% by weight, preferably in an amount of from 1% by weight to 40% by weight, particularly preferably in an amount of from 5% by weight to 20% by weight, of the total oil phase consisting of A) and G), where the % by weight refer to the total microemulsion, except in the case of component G).

The present invention further provides a process for the preparation of a microemulsion according to the invention, comprising the process steps

- I) provision of at least one polysiloxane as described above,
- II) optional dissolution of the polysiloxane with at least one solvent E) and/or a nonionic surfactant of component B) and/or oil G),
- III) addition of the remaining components forming the microemulsion, the components water and preservative being added last.

The components A) to G) described in the process according to the invention correspond to the components described above in connection with the microemulsions according to the invention, with respectively preferred components of the microemulsions obviously being used with preference in the process according to the invention; for the sake of completeness, it may be explained that this statement naturally applies to the amounts of individual components used.

In the process according to the invention, strong mechanical forces do not have to be applied in order to form an emulsion since microemulsions are emulsions that are formed spontaneously; nevertheless, it is preferred according to the invention that during all of the process steps I)-III), mixing is carried out with a simple stirrer, such as, for example, a pendulum stirrer.

In processes preferred according to the invention, polysiloxanes described as preferred above in connection with the microemulsions according to the invention are preferably used.

In order to avoid any high-viscosity states that may arise during the preparation of the microemulsion, it may be advantageous if the process according to the present invention is characterized in that process steps I)-III) are carried out at slightly elevated temperature, for example in a temperature range from 21° C. to 90° C., in particular from 30° C. to 50° C.

The microemulsions of the present invention can advantageously be used for producing care and cleaning formulations, in particular for skin and skin appendages, such as for example conditioners for hair, as well as care and cleaning formulations for the home and industry, these preferably being selected from the group of cosmetic, cleaning and care formulations. Consequently, uses of this type are likewise provided by the present invention.

The term "care formulation" is understood here as meaning a formulation which fulfils the purpose of restoring an object to its original form, of reducing or preventing the effects of external influences (e.g. time, light, temperature, pressure, soiling, chemical reaction with other reactive compounds that come into contact with the object) such as, for example, ageing, soiling, material fatigue, bleaching, or even of improving desired positive properties of the object. For the last point, improved hair shine or greater elasticity of the object under consideration may be mentioned.

In this connection, the care and cleaning formulations are not limited to cosmetic, pharmaceutical or dermatological formulations such as e.g. for the treatment of hair in the form of hair shampoos, 2-in-1 shampoos, liquid soaps, hair rinses, permanent wave neutralizing solutions, hair colouring shampoos, hair-setting compositions, hair treatments, hair-arranging compositions, hair-styling preparations, blow-drying lotions, setting foams, hair treatments, leave-in conditioners, hair-smoothing compositions, shine-improving compositions and compositions for colouring the hair, as well as other cleaning and grooming formulations, but may also be those formulations as are used in the home and industry, for exmaple for the care and cleaning of surfaces of inanimate objects such as, for example, tiles, wood, glass, ceramic, linoleum, plastic, painted surfaces, leather, materials, fibres. Examples of such objects are window panes and sills, shower dividers, floorings such as carpets, tiles, laminate, parquet, cork floorings, marble, stone and fine stoneware floors, household ceramics such as WCs, wash basins, bidets, shower trays, bath tubs, door handles, fittings, household appliances such as washing machines, driers, dishwashers, dishes made of ceramic or stainless steel, furniture such as tables, chairs, shelves, worktops, windows, cooking utensils, crockery and cutlery, laundry, in particular laundry worn close to the body ("undergarments"), water-borne vessels, vehicles and aircraft such as cars, buses, motorboats and sailing boats, articles such as surgical instruments, vacuum cleaners, engines, pipelines, tanks and devices for transportation, processing and storage in food processing. This is thus in this connection the use in cleaning and care compositions for the home, industrial and institutional trade.

In this connection, the surface to be cared for and cleaned is preferably that of a fibre or of a textile, in particular the surface of woven textiles, laundry, upholstery or carpets. This invention further provides the use of the microemulsions according to the invention as conditioners for hair-treatment compositions and hair aftertreatment compositions and also as compositions for improving the hair structure.

The present invention thus also further provides the care and cleaning formulations, in particular for skin and skin appendages, and also of care and cleaning formulations for the home and industry, in particular cosmetic formulations, these preferably being selected from the group of hair-treatment compositions and hair aftertreatment compositions for rinsing out or for leaving in the hair, for example shampoos with or without a marked conditioning effect, 2-in-1 shampoos, rinses, hair treatments, hair masks, styling aids, styling compositions, blow-drying lotions, hair-setting compositions, permanent-waving compositions, hair-smoothing compositions and compositions for colouring the hair, in particular conditioners and shampoos comprising at least one microemulsion according to the invention. Cosmetic formulations that are particularly preferred according to the invention are themselves also essentially free from alkoxylated compounds.

Preferred cleaning and care formulations according to the invention for the home, industrial and institutional applications comprising at least one of the microemulsions according to the invention are disinfectants, disinfectant cleaners, foam cleaners, floor cleaners, carpet cleaners, upholstery cleaners, floor care products, marble cleaners, parquet cleaners, stone and ceramic floor cleaners, wipe care compositions, stainless steel cleaners, glass cleaners, dishwashing detergents, plastics cleaners, sanitary cleaners, wool cleaners, leather cleaners, detergents, laundry care compositions, disinfectant detergents, universal detergents, gentle detergents, wool detergents, fabric softeners and impregnation compositions, with particular preference being given to detergents, laundry care compositions, universal detergents, gentle detergents, wool detergents, fabric softeners, impregnation compositions, in particular fabric softeners. Particularly preferred cleaning and care formulations according to the invention for the home, industrial and institutional applications comprising at least one of the microemulsions according to the invention are textile-care formulations for the repeated cleaning and care of textiles and fabrics. In this connection, a textile-care formulation is understood as meaning any formulation which imparts to the textile structures treated therewith an advantageous effect, such as, for example, a textile-softening effect, crease resistance and/or reduces the harmful or negative effects which can arise during cleaning and/or conditioning and/or wearing, such as, for example, fading, greying, etc. It is particularly preferred for the textile-care formulation to be a textile-softening formulation (fabric softener).

Textile-softening formulations (fabric softeners) are in particular aqueous (i.e. with a weight fraction of at least 5% by weight of water, based on the total formulation) formulations which contain, as main effective constituent, one or more cationic textile-softening compound which have one or more long-chain alkyl groups in a molecule. Widespread cationic textile-softening compounds include for example methyl N-(2-hydroxyethyl)-N,N-di(tallowacyloxyethyl)ammonium compounds or N,N-dimethyl-N,N-di(tallowacyloxyethyl) ammonium compounds. Further suitable ammonium compounds are disclosed in US 2010/0184634 in paragraphs [0027] to [0068], the explicit disclosure content of which in this regard forms part of this disclosure by virtue of this reference. The textile-softening formulations can, moreover, comprise further additives and auxiliaries, in particular perfume, dyes, viscosity regulators, defoamers, preservatives, organic solvents, non-siloxane-containing polymers and other siloxane-containing polymers. In particular, the textile-softening formulations can comprise between 0.001 and 25, particularly preferably 0.01 to 15% by weight, of one or more different additives or auxiliaries, the % by weight referring to the total formulation.

As perfume, all fragrances or fragrance mixtures known to be suitable from the prior art for textile-softening formulations are used, preferably in the form of a perfume oil. Examples of fragrances or odorants are disclosed inter alia in DE 197 51 151 A1, page 4, lines 11-17. In particular, the textile-softening formulations can comprise between 0.01 and 10, particularly preferably 0.1 to 5% by weight, of one or more fragrances or fragrance mixtures, the % by weight referring to the total formulation.

Dyes which can be used are all of the dyes known to be suitable from the prior art for textile-softening formulations, with water-soluble dyes being preferred. Examples of suitable water-soluble dyes are SANDOLAN® Walkblau NBL 150 (manufacturer Clariant) and Sicovit® Azorubin 85 E122 (manufacturer BASF). In particular, the textile-softening formulations can comprise between 0.001 and 0.1% by weight, particularly preferably 0.002 to 0.05% by weight, of one or more dyes or dye mixtures, with the % by weight referring to the total formulation.

As viscosity regulator for reducing the viscosity, the textile-softening formulation can comprise an alkali metal or alkaline earth metal salt, preferably calcium chloride, in an amount of 0.05-2% by weight, where the % by weight refer to the total formulation. As viscosity regulator for increasing the viscosity, the textile-softening formulation can comprise a thickener known to be suitable from the prior art, with the polyurethane thickeners known from WO 2007/125005 being preferred. Examples of suitable thickeners are TEGO® Visco Plus 3030 (manufacturer Evonik Tego Chemie), Acusol® 880 and 882 (manufacturer Rohm & Haas), Rheovis® CDE (manufacturer BASF), Rohagit® KF 720 F (manufacturer Evonik Röhm GmbH) and Polygel® K100 from Neochem GmbH.

Defoamers which can be used are all defoamers known to be suitable from the prior art for textile-softening formulations. Examples of suitable standard commercial defoamers are Dow Corning® DB-110A and TEGO® Antifoam® 7001 XP. In particular, the textile-softening formulations can comprise between 0.0001 and 0.05, particularly preferably 0.001 to 0.01% by weight, of one or more different defoamers, with the % by weight referring to the total formulation.

As preservatives, the textile-softening formulation can comprise bactericidal and/or fungicidal active ingredients known to be suitable from the prior art, with water-soluble active ingredients being preferred. Examples of suitable standard commercial bactericides are methylparaben, 2-bromo-2-nitro-1,3-propanediol, 2-methyl-4-isothiazolin-3-one and 5-chloro-2-methyl-4-isothiazolin-3-one. The textile-softening formulation can likewise comprise an oxidation inhibitor as preservative. Examples of suitable standard commercial oxidation inhibitors are ascorbic acid, 2,6-di-tert-butyl-4-methlyphenol (BHT), butylhydroxyanisole (BHA), tocopherol and propyl gallate. In particular, the textile-softening compositions can comprise between 0.0001 and 0.5, particularly preferably 0.001 to 0.2% by weight, of one or more different preservatives. In particular, the textile-softening formulation can comprise between 0.001 and 0.1, particularly preferably 0.001 to 0.01% by weight, of one or more different oxidation inhibitors, with the % by weight referring to the total formulation.

As organic solvents, the textile-softening formulation can comprise short-chain alcohols, glycols and glycol monoethers, with ethanol, 2-propanol, 1,2-propanediol and dipropylene glycol being preferred. In particular, the textile-softening compositions can comprise between 0.1 and 10, particularly preferably 0.2 to 5% by weight, of one or more different organic solvents, with the % by weight referring to the total formulation. The textile-softening formulation can comprise one or more non-siloxane-containing polymers. Examples thereof are carboxymethylcellulose, polyethylene glycol, polyvinyl alcohol, poly(meth)acrylates, polyethyleneimines or polysaccharides. In particular, the textile-softening formulations can comprise between 0.01 and 25, particularly preferably 0.1 to 10% by weight, of one or more different non-siloxane-containing polymers, with the % by weight referring to the total formulation.

Moreover, the textile-softening formulation can comprise further additives, not listed here, which are obvious to the person skilled in the art or are prior art.

The invention further provides the use of the microemulsions according to the invention in textile-care detergents or cleaners. As a result of incorporation into a detergent or cleaner, the consumer is provided with a textile-care detergent or cleaner ("2-in-1" detergent or cleaner) and he does not need to dose two compositions (detergent or cleaner and fabric softener), as well as no separate rinse cycle. In addition to the textile-care formulation and the surfactants, the textile-care detergents or cleaners can comprise further ingredients which further improve the application-related and/or aesthetic properties of the detergent or cleaner. Preferred detergents or cleaners additionally comprise one or more substances from the group of surfactants, builders, bleaches, bleach activators, enzymes, perfumes, perfume carriers, fluorescent agents, dyes, foam inhibitors, silicone oils, antiredeposition agents, optical brighteners, greying inhibitors, shrink preventers, crease protectants, colour transfer inhibitors, antimicrobial active ingredients, germicides, fungicides, antioxidants, preservatives, corrosion inhibitors, antistats, bittering agents, ironing aids, phobization and impregnation agents, swelling agents and antislip agents, neutral filling salts, and also UV absorbers. In particular, the textile-care detergents or cleaners according to the invention can comprise between 0.001 and 90, particularly preferably 0.01 to 45% by weight, of one or more of the further ingredients mentioned here, with the % by weight referring to the total formulation.

Examples of surfactants that can be used are described in WO 2007/115872, page 17, line 28 to page 21, line 24. Examples of builder materials, builders, bleaches, bleach activators, bleach catalysts and enzymes are described in WO 2007/115872, page 22, line 7 to page 25, line 26. Antiredeposition agents, optical brighteners, greying inhibitors, colour transfer inhibitors are described for example in WO 2007/115872 on page 26, line 15 to page 28, line 2. Examples of crease protectants, antimicrobial active ingredients, germicides, fungicides, antioxidants, preservatives, antistats, ironing aids, UB absorbers are described in WO 2007/115872 on pages 28, line 14 to page 30, line 22. Their explicit disclosure content in this regard forms part of this disclosure by virtue of this reference.

A formulation preferred according to the invention comprises the microemulsion according to the invention in an amount of from 0.1% by weight to 99% by weight, preferably in an amount of from 0.5% by weight to 20% by weight, particularly preferably in an amount of from 1.0% by weight to 10% by weight, the % by weight referring to the total formulation.

The formulation according to the invention, in particular the cosmetically formulation, can for example comprise at least one additional component selected from the group of
emollients,
emulsifiers,
thickeners/viscosity regulators/stabilizers,
antioxidants,
hydrotropes (or polyols),
solids and fillers,
pearlescent additives,
deodorant and antiperspirant active ingredients,
insect repellents,
self-tanning agents,
preservatives,
conditioners,
perfumes,
dyes,
cosmetic active ingredients,
care additives,
superfatting agents
solvents.

Substances which can be used as exemplary representatives of the individual groups are known to the person skilled in the art and can be found for example in EP2273966A1. This patent application is hereby incorporated by reference and thus forms part of the disclosure.

As regards further optional components and the amounts used of these components, reference is made expressly to the relevant handbooks known to the person skilled in the art, for example K. Schrader, "Grundlagen and Rezepturen der Kosmetika" [Fundamentals and Formulations of Cosmetics], 2nd Edition, page 329 to 341, HUthig Buch Verlag Heidelberg.

The invention further provides the use of the microemulsions according to the invention as additive for coatings and paints, in particular for water-based coatings and paints, preferably those in which polyurethane dispersions are used as binders. By adding the microemulsion, the user is given coatings and paints which, following application, are characterized by lower (stick-)slip friction and altered feel or haptics.

Coatings and paints, in particular for the coating of textile, metal, leather, plastic, paper, cardboard and wood, comprising at least one microemulsion according to the invention or at least one microemulsion obtainable by the process according to the invention, where these coatings and paints preferably comprise an aqueous polyurethane dispersion as binder, are likewise provided by the present invention.

In addition to the binder and the microemulsion according to the invention, the coating or the paint can comprise further ingredients which further improve the application-related and/or aesthetic properties of the coating. Preferred coating systems additionally comprise one or more substances from the group of primary binders or cobinders, crosslinkers, curing agents, surfactants, substrate wetting agents, dispersion additives, rheology additives, defoamers, deaerators, and also inorganic or else also organic pigments, dyes, slip and flow additives, fillers, matting agents, bead polymers, natural and synthetic waxes, grip-improving agents, antimicrobial active ingredients, germicides, fungicides, antioxidants, preservatives, UV stabilizers and polar solvents.

Coatings or paints preferred according to the invention comprise the microemulsion according to the invention in an amount of from 0.1% by weight to 99% by weight, preferably in an amount of from 0.5% by weight to 20% by weight, particularly preferably in an amount of from 1.0% by weight to 10% by weight, with the % by weight referring to the total formulation.

The amounts of the particular additives are governed by the intended use. Typical guide formulations for the respective applications are known prior art and are contained for example in the brochures of the manufacturers of the particular base materials and active ingredients. These existing formulations can as a rule be adopted unchanged. If necessary, the desired modifications, however, can be undertaken without complication by simple experiments for the purposes of adaptation and optimization.

In the examples listed below, the present invention is described by way of example, without there being any intention of limiting the invention, the scope of application of which arises from the entire description and the claims, to the embodiments given in the examples.

FIG. 1 is part of the examples and shows the lowering of the friction as a result of using conditioners.

EXAMPLES

Siloxane 1

Polysiloxane T-Quat with N=121

A quaternary polysiloxane was prepared according to Example 4 from EP 1887024, but with a total siloxane chain length of N=121. This gave a high-viscosity, slightly yellowish product with the following statistical structure.

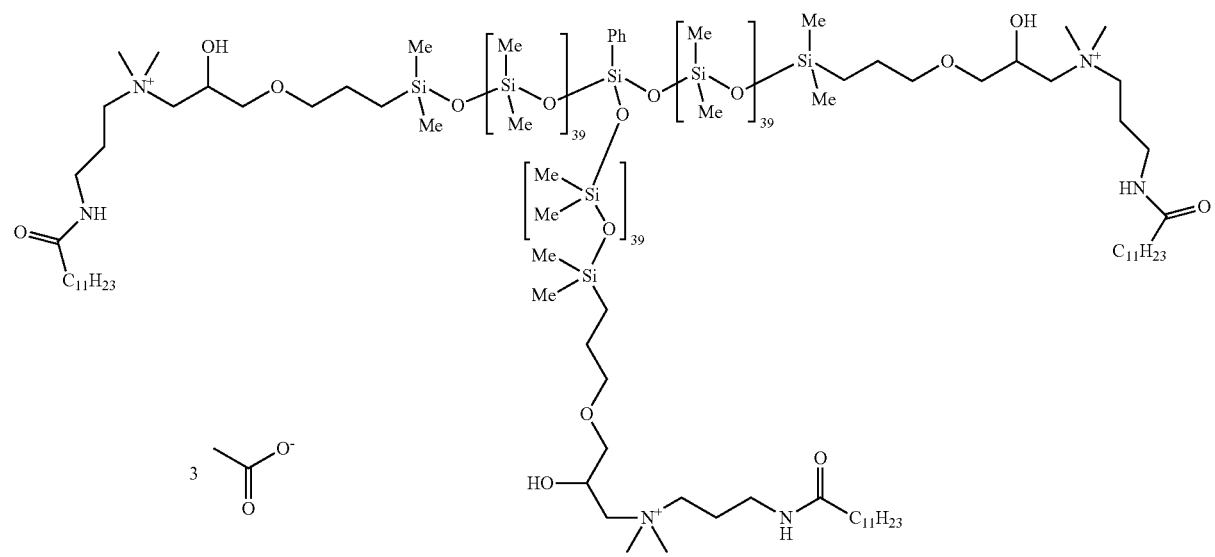

Siloxane 2

Polysiloxane T-Quat with N=151

A quaternary polysiloxane was prepared according to Example 4 from EP 1887024, but with a total siloxane chain length of N=151 and with lactic acid instead of acetic acid. This gave a high-viscosity, slightly yellowish product with the following statistical structure.

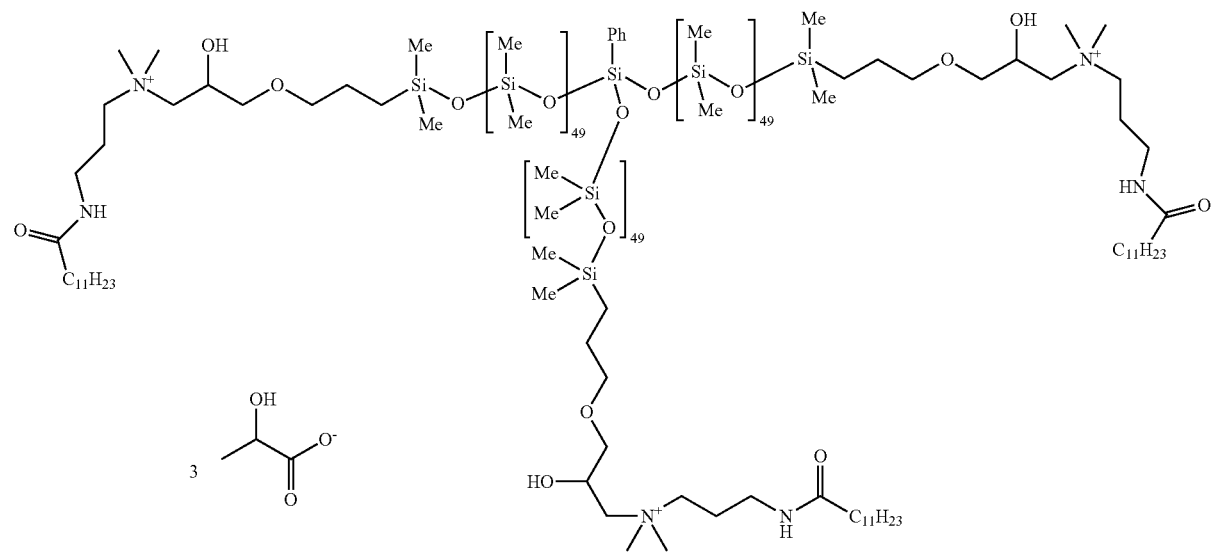

Siloxane 3

Polysiloxane T-Quat with N=211

A quaternary polysiloxane was prepared according to Example 4 from EP 1887024, but with a total siloxane chain length of N=211. This gave a high-viscosity, slightly yellowish product having the following statistical structure.

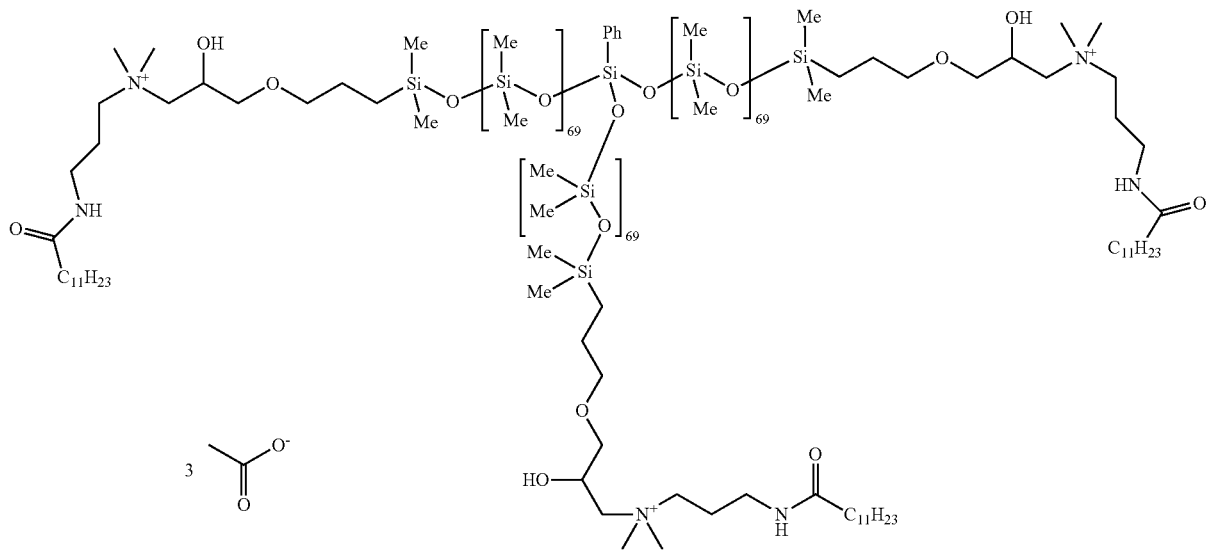

Siloxane 4

Polysiloxane Multi-T-Quat with N=250

A quaternary polysiloxane with 5 T units was prepared according to Example 2 from PCT/EP2010/070071, but with a total siloxane chain length of N=250. This gave a very viscous, yellowish product having the following statistical formula.

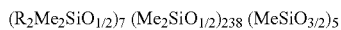

where $R_2$ =

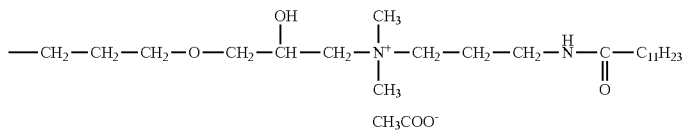

Siloxane 5

Polysiloxane Multi-T-Quat with N=350

A quaternary polysiloxane with 5 T units was prepared according to Example 2 from PCT/EP2010/070071, but with a total siloxane chain length of N=350. This gave a clear, very viscous, yellowish product having the following statistical formula.

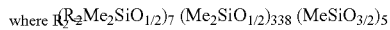

where $R_2$ =

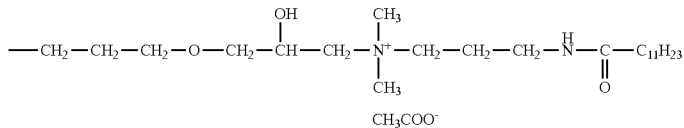

Siloxane 6

Polysiloxane T-Quat with N=61

A quaternary polysiloxane was prepared according to Example 4 from EP 1887024, but with a total siloxane chain length of N=61. This gave a high-viscosity, slightly yellowish product having the following statistical structure.

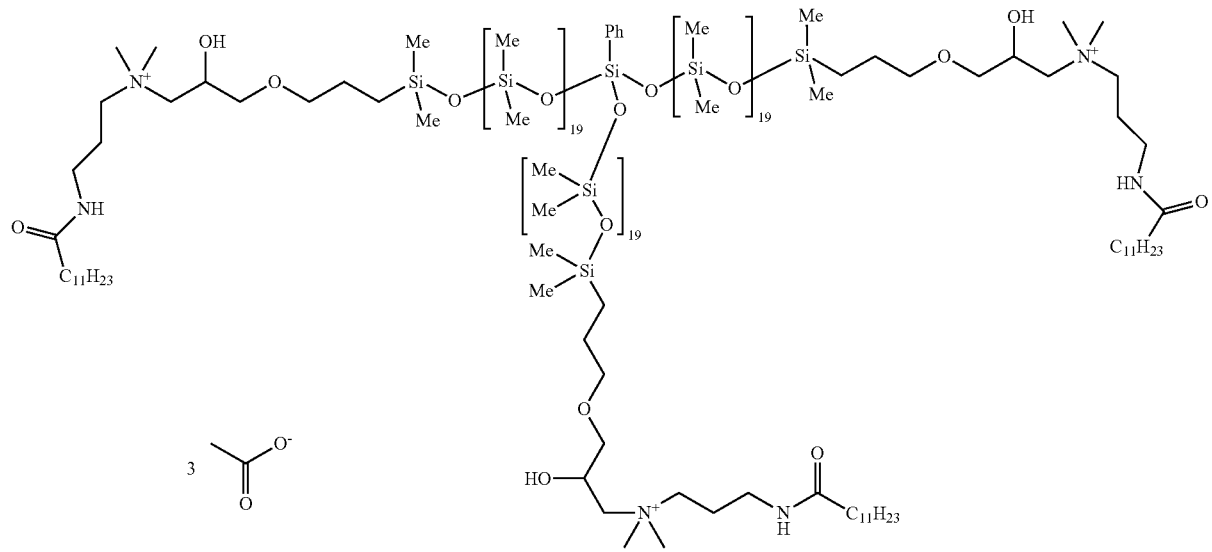

Formulation Examples of Microemulsions

| Constituent | ME1 | ME2 | ME3 |
|---|---|---|---|
| | | % by weight | |
| Siloxane 2 | 25.02 | 21.20 | 27.90 |
| VARISOFT ® 300, Evonik Goldschmidt GmbH (Cetrimonium Chloride) | 9.18 | 10.23 | 5.68 |
| ANTIL ® Soft SC, Evonik Goldschmidt GmbH (Sorbitan Sesquicaprylate) | 7.63 | | |
| Imbentin ® U/050, Kolb (Undeceth-5) | | 9.96 | |
| Dermosoft ® GMCY, Dr. Straetmans (Glyceryl Caprylate) | | | 11.25 |
| Isopropanol | 6.23 | 5.30 | |
| DOWANOL ® TPM, Dow Chemical (Tripropylene glycol monomethyl ether) | | | 6.97 |
| Water | 51.94 | 53.31 | 48.20 |

| Constituent/% by weight | ME4 | ME5 | ME6 | ME7 |
|---|---|---|---|---|
| Siloxane 2 | 25.70 | 31.00 | 30.00 | 30.00 |
| Dipropylene glycol | 8.10 | 2.10 | 5.00 | 10.00 |
| Dermosoft ® GMCY, Dr. Straetmans (Glyceryl Caprylate) | 7.70 | 9.50 | 9.00 | 9.10 |
| Glycerol | 10.40 | | | |
| VARISOFT ® 300, Evonik Goldschmidt GmbH (Cetrimonium Chloride) | 2.50 | | 3.50 | |
| VARISOFT ® PATC, Evonik Goldschmidt GmbH (Palmitamidopropyltrimonium Chloride) | | 3.20 | | 3.50 |
| Phenoxyethanol | 0.80 | 0.90 | 0.80 | 0.80 |
| Water | 44.10 | 53.00 | 51.40 | 46.40 |
| Capric acid | 0.40 | | | |
| Citric acid 40% strength | 0.30 | | | |
| NaCl | | 0.30 | 0.30 | 0.20 |

| Constituent | ME8 | ME9 |
|---|---|---|
| | % by weight | |
| Siloxane 2 | 30.00 | 30.00 |
| 1,2-Hexanediol | 4.80 | |
| Hexylene glycol | | 8.20 |
| Glyceryl caprylate | 6.30 | 9.20 |
| VARISOFT ® PATC, Evonik Goldschmidt GmbH (Palmitamidopropyltrimonium Chloride) | 5.00 | 3.60 |
| Phenoxyethanol | 0.80 | 0.80 |
| Water | 53.10 | 48.20 |

| Constituent | ME10 | ME11 |
|---|---|---|
| | % by weight | |
| Siloxane 2 | 25.20 | 26.00 |
| Dipropylene glycol | | 10.30 |

| Constituent | % by weight | |
|---|---|---|
| | ME10 | ME11 |
| Hexylene glycol | 8.00 | |
| Dermosoft ® GMCY, Dr. Straetmans (Glyceryl Caprylate) | 9.20 | |
| Glyceryl caprylate | | 6.20 |
| TEGO ® Retain F50, Evonik Goldschmidt GmbH (Cocoamidopropylbetaine) | | 5.20 |
| VARISOFT ® PATC, Evonik Goldschmidt GmbH (Palmitamidopropyltrimonium Chloride) | 3.60 | 3.90 |
| Phenoxyethanol | 0.80 | 0.80 |
| Water | 53.20 | 47.60 |

| Constituent | % by weight | | |
|---|---|---|---|
| | ME12 | ME13 | ME14 |
| Siloxane 2 | 30.36 | 28.20 | 25.57 |
| Propylene glycol | 10.12 | | |
| Hexylene glycol | | 9.40 | |
| Butylene glycol | | | 8.52 |
| Glyceryl caprylate | 6.07 | 5.60 | 5.30 |
| TEGO ® Betain F50, Evonik Goldschmidt GmbH (Cocoamidopropylbetaine) | 10.12 | 9.40 | 8.90 |
| VARISOFT ® PATC, Evonik Goldschmidt GmbH (Palmitamidopropyltrimonium chloride) | 4.05 | 3.80 | 3.60 |
| Phenoxyethanol | 0.81 | 0.80 | 0.76 |
| Water | 38.47 | 42.80 | 47.35 |

| Constituent | % by weight | | |
|---|---|---|---|
| | ME15 | ME16 | ME17 |
| Siloxane 1 | 25.62 | 30.00 | |
| Siloxane 6 | | | 30.03 |
| Dipropylene glycol | | 10.00 | 5.01 |
| Dermosoft ® GMCY, Dr. Straetmans (Glyceryl Caprylate) | 9.67 | 9.00 | 9.01 |
| Glycerol | 13.84 | | |
| Capric acid | 0.64 | | |
| VARISOFT ® PATC, Evonik Goldschmidt GmbH (Palmitamidopropyltrimonium chloride) | 3.33 | 3.50 | 3.50 |
| Phenoxyethanol | 0.83 | 0.80 | 0.80 |
| Water | 46.07 | 46.47 | 51.39 |
| NaCl | | 0.23 | 0.26 |

| Constituent | % by weight | | | |
|---|---|---|---|---|
| | ME18 | ME19 | ME20 | ME21 |
| Siloxane 2 | 30.00 | 40.12 | 46.30 | |
| Siloxane 5 | | | | 30.00 |
| Dipropylene glycol | 9.00 | 7.08 | 14.81 | |
| Propylene glycol | | | | 10.00 |
| TEGOSOFT ® PC 31, Evonik Goldschmidt GmbH (Polyglyceryl-3 Caprate) | 11.00 | 10.00 | 12.22 | 10.00 |
| TEGO ® Betain F 50, Evonik Goldschmidt GmbH (Cocoamdopropyl Betaine) | 10.00 | 10.00 | 4.63 | 5.00 |
| VARISOFT ® PATC, Evonik Goldschmidt GmbH (Palmitamidopropyltrimonium chloride) | 3.60 | 3.60 | 1.48 | 2.40 |
| Water | 36.40 | 29.20 | 20.56 | 42.6 |

| Constituent | % by weight | | | |
|---|---|---|---|---|
| | ME22 | ME23 | ME24 | ME25 |
| Siloxane 2 | 26.19 | 24.11 | 30.31 | 33.04 |
| Dipropylene glycol | 13.15 | 11.87 | | |
| 1,2-Hexanediol | | | 14.43 | 15.22 |
| Dermosoft ® GMCY, Dr. Straetmans (Glyceryl Caprylate) | 10.66 | | | |
| TEGOSOFT ® CT, Evonik Goldschmidt GmbH (Caprylic/Capric Triglyceride) | | | 3.00 | |
| TEGOSOFT ® M, Evonik Goldschmidt GmbH (Isopropyl Myristate) | | 7.45 | | 1.22 |
| VARISOFT ® 432 PPG, Evonik Goldschmidt GmbH (Dicetyldimonium chloride) | 3.71 | 16.23 | 5.77 | 3.52 |
| Water | 46.29 | 40.34 | 46.49 | 47.00 |

| Constituent | % by weight | | | |
|---|---|---|---|---|
| | ME26 | ME27 | ME28 | ME29 |
| Siloxane 2 | 28.85 | 27.08 | 35.62 | 26.87 |
| Dipropylene glycol | 5.77 | 13.02 | | 13.33 |
| Butyl diglycol | | | 10.27 | |
| Dermosoft ® GMCY, Dr. Straetmans (Glyceryl Caprylate) | | | | 10.66 |
| ANTIL ® Soft SC, Evonik Goldschmidt GmbH (Sorbitan Sesquicaprylate) | | 10.42 | | |
| TEGO ® Cosmo P 813, Evonik Goldschmidt GmbH (Polyglyceryl-3-Caprylate) | 9.62 | | | |
| CAPRYOL 90 ™, Gattefossé (Propylene Glycol Monocaprylate) | | | 10.27 | |
| TEGO ® Betain F 50, Evonik Goldschmidt GmbH (Cocoamdopropyl Betaine) | 5.77 | | | |
| VARISOFT ® 432 CG, Evonik Goldschmidt GmbH (Dicetyldimonium Chloride) | | | | 3.72 |

-continued

| | % by weight | | | |
|---|---|---|---|---|
| Constituent | ME26 | ME27 | ME28 | ME29 |
| VARISOFT ® PATC, Evonik Goldschmidt GmbH (Palmitamidopropyltrimonium chloride) | 2.30 | 5.21 | 6.85 | |
| Water | 47.69 | 44.27 | 36.99 | 45.42 |

| | % by weight | | | | |
|---|---|---|---|---|---|
| Constituent | ME30 | ME31 | ME32 | ME33 | ME34 |
| Siloxane 2 | 24.11 | | | | |
| Siloxane 1 | | | | | 38.46 |
| Siloxane 3 | | | 14.80 | | |
| Siloxane 4 | | 30.00 | | | |
| Siloxane 5 | | | | 20.50 | |
| TEGO ® Alkanol TD6, Evonik Goldschmidt GmbH (POE-(6)-isotridecyl Alcohol) | 8.74 | 12.00 | 12.00 | 11.80 | 11.54 |
| Water | 58.65 | 49.60 | 64.80 | 59.30 | 28.85 |
| Isopropanol | 8.50 | 8.40 | 8.40 | 8.40 | 21.15 |

| | % by weight | |
|---|---|---|
| Constituent | ME35 | ME36 |
| Siloxane 2 | 21.1 | |
| Siloxane 5 | | 20.0 |
| TEGO ® Alkanol TD6, Evonik Goldschmidt GmbH (POE-(6)-isotridecyl Alcohol) | 11.6 | 12.00 |
| Lutensol TO12, BASF AG (POE-(12)-isotridecyl Alcohol) | 3.8 | 3.8 |
| Water | 58.2 | 56.2 |
| Dipropylene glycol | 5.3 | 8.0 |

Cosmetics Applications Technology:

Hereinbelow 4 different products were tested in cosmetic formulations:

The microemulsion ME18 according to the invention has the following composition (see above):

| Constituent/% by weight | ME18 |
|---|---|
| Siloxane 2 | 30.00 |
| Dipropylene glycol | 9.00 |
| TEGOSOFT ® PC 31, Evonik Goldschmidt GmbH (Polyglyceryl-3 Caprate) | 11.00 |
| TEGO ® Betain F 50, Evonik Goldschmidt GmbH (Cocoamdopropyl Betaine) | 10.00 |
| VARISOFT ® PATC, Evonik Goldschmidt GmbH (Palmitamidopropyltrimonium Chloride) | 3.60 |
| Water | 36.40 |

The microemulsion has a silicone active ingredient content of 30%.

Comparative Example Product 2 (not According to the Invention)

For this, siloxane 2 was dissolved in 15% dipropylene glycol (i.e. active content of 85% silicone active ingredient).

Comparative Example 3 (not According to the Invention)

Amino-group-containing siloxane DC2-8566 (commercially available from Dow Corning, INCI: Amodimethicone). The product consists of 100% silicone active ingredient.

Comparative Example 4 (not According to the Invention)

Microemulsion with quaternary siloxane DC5-7113 (commercially available from Dow Corning, INCI: Silicone Quaternium-16 (and) Undeceth-11 (and) Butyloctanol (and) Undeceth-5). The microemulsion has a silicone active ingredient content of 22%.

Application-Related Properties

The formulation constituents are named in the compositions in the form of the generally recognized INCI nomenclature using the English terms. All of the concentrations in the application examples are given in percent by weight.

1.) Testing the Conditioning of Skin (Skin Care Benefit) and the Foam Properties by Means of a Hand Washing Test:

To assess the conditioning of skin (skin care benefit) and the foam properties of the microemulsion ME18 according to the invention in aqueous, surface-active formulations, sensory hand washing tests were carried out in comparison to the Comparative Examples 2 and 3 according to the prior art.

Comparative Example 3 is widespread in the industry as care active ingredient and is considered to be a highly effective care active ingredient in aqueous, surface-active formulations.

Comparative Example 2 contains the same silicone active ingredient as the microemulsion ME18.

A group consisting of 10 trained test subjects washed their hands in a defined manner and evaluated foam properties and skin feel using a grading scale from 1 (poor) to 5 (very good).

The products used were tested in each case in a standardized surfactant formulation (Table 1).

As control formulation 0b, a formulation without the addition of an organomodified siloxane is used.

TABLE 1

| Test formulations for hand washing test | | | | |
|---|---|---|---|---|
| Formulation examples | 0b | 1b | C2b | C3b |
| Texapon NSO ®, 28% strength, Cognis (INCI: Sodium Laureth Sulfate) | 32% | 32% | 32% | 32% |
| TEGO ® Betain F 50, 38% strength, Evonik Goldschmidt GmbH (INCI: Cocamidopropyl Betaine) | 8% | 8% | 8% | 8% |
| NaCl | 2% | 2% | 2% | 2% |
| Water, demineralized | | ad 100.0% | | |
| Microemulsion ME18 (according to the invention) | | 1.67% | | |
| Comparative Example 2 (not according to the invention) | | | 0.59% | |
| Comparative Example 3 (not according to the invention) | | | | 0.5% |

Testing with formulation example C2b could not take place since considerable separation occurred. The silicone active ingredient cannot be stably incorporated into the surface-active formulation.

The sensory test results are summarized in Table 2.

TABLE 2

Results of the hand washing test

| Test formulation | 0b | 1b | C3b |
|---|---|---|---|
| Foaming behaviour | 3.0 | 4.0 | 3.3 |
| Foam volume | 2.8 | 3.5 | 2.9 |
| Foam creaminess | 2.3 | 3.2 | 3.0 |
| Skin feel during washing | 2.8 | 4.0 | 3.7 |
| Skin smoothness | 1.4 | 3.5 | 2.9 |
| Skin softness | 2.0 | 3.3 | 2.9 |
| Skin smoothness after 3 min | 2.6 | 3.9 | 3.6 |
| Skin softness after 3 min | 2.5 | 3.8 | 3.5 |

Table 2 shows the results of the hand washing test. It is evident from the measurement results that formulation 1b according to the invention using microemulsion ME18 according to the invention is superior in all application properties compared to comparison formulation C2b according to the prior art.

Against this background, the results of formulation 1b according to the invention are to be deemed as very good.

It is evident from the measurement values that microemulsion ME18 according to the invention leads in formulation 1b to an improvement in the skin properties and foam properties compared to comparative example 3 in formulation C3b.

Furthermore, the measurement values reveal that the control formulation 0b without a silicone compound has poorer measurement values than formulations 1b and C3b.

Furthermore, the fact that comparative example 2 cannot be incorporated into comparative formulation C2b, although comparative example 2 contains the same silicone active ingredient as microemulsion ME18 according to the invention, is clear evidence for the fact that the microemulsions according to the invention represent a considerable improvement of the prior art since the microemulsions according to the invention permit the use of silicone active ingredients which have not been able to be used according to the prior art in surface-active formulations.

2.) Testing the Conditioning of Hair by Means of Sensory Tests:

For the application-related assessment of the conditioning of hair, microemulsion ME18 according to the invention and comparative example 3 were used in simple cosmetic formulations (shampoo and hair rinse).

The application properties upon use in a shampoo were tested in the following formulations:

TABLE 3

Shampoo formulations for testing the hair conditioning properties.

| Formulation examples | 0c | 1c | C2c |
|---|---|---|---|
| Texapon NSO ®, 28% strength, Cognis (INCI: Sodium Laureth Sulfate) | 32% | 32% | 32% |
| TEGO ® Betain F 50, 38% strength, Evonik Goldschmidt GmbH (INCI: Cocamidopropyl Betaine) | 8% | 8% | 8% |
| Jaguar 162, Rhodia (INCI: Guar Hydroxypropyl trimonium Chloride) (Cationic polymer for improving the effectiveness of conditioners) | 0.3% | 0.3% | 0.3% |
| Water, demineralized | ad 100.0% | | |
| Citric acid | ad pH 6.0 ± 0.3 | | |
| Microemulsion ME18 (according to the invention) | | 1.67% | |

TABLE 3-continued

Shampoo formulations for testing the hair conditioning properties.

| Formulation examples | 0c | 1c | C2c |
|---|---|---|---|
| Comparative Example 3 (not according to the invention) | | | 0.5% |

To assess the properties of the shampoo formulation, no after-treatment with a rinse was carried out in the course of the test.

The application properties upon use in hair rinses were tested in the following formulations:

TABLE 4

Hair rinse formulations for testing the hair conditioning properties.

| Formulation examples | 0d | 1d | C2d |
|---|---|---|---|
| TEGINACID ® C, Evonik Goldschmidt GmbH (INCI: Ceteareth-25) | 0.5% | 0.5% | 0.5% |
| TEGO ® Alkanol 16, Evonik Goldschmidt GmbH (INCI: Cetyl Alcohol) | 4% | 4% | 4% |
| VARISOFT ® 300, 30% strength, Evonik Goldschmidt GmbH (INCI: Cetrimonium Chloride) | 3.3% | 3.3% | 3.3% |
| Water, demineralized | ad 100.0% | | |
| Citric acid | ad pH 4.0 ± 0.3 | | |
| Microemulsion ME18 (according to the invention) | | 1.67% | |
| Comparative Example 3 (not according to the invention) | | | 0.5% |

In the case of the property testing of hair rinses, the hair is pretreated using a shampoo which contains no conditioner.

For the application-related assessment, hair tresses which are used for sensory tests are predamaged in a standardized manner by means of a permanent wave treatment and a bleaching treatment. For this, standard hairdressing products are used. The test procedure, the base materials used, and also the details of the assessment criteria are described in DE 103 27 871.

Standardized Treatment of Predamaged Hair Tresses with Conditioning Samples:

The hair tresses predamaged as described above are treated as follows with the above-described shampoo or the above-described conditioning rinse:

The hair tresses are wetted under running warm water. The excess water is gently squeezed out by hand, then the shampoo is applied and gently worked into the hair (1 ml/hair tress (2 g)). After a residence time of 1 min, the hair is rinsed for 1 min.

Where appropriate, directly afterwards the rinse is applied and gently worked into the hair (1 ml/hair tress (2 g)). After a residence time of 1 min, the hair is rinsed for 1 min.

Prior to the sensory assessment, the hair is dried in the air at 50% atmospheric humidity and 25° C. for at least 12 h.

Assessment Criteria:

The sensory evaluations are made according to grades awarded on a scale from 1 to 5, with 1 being the poorest evaluation and 5 being the best evaluation. The individual test criteria are each given their own evaluation.

The test criteria are: wet combability, wet feel, dry combability, dry feel, appearance/shine.

The table below compares the results of the sensory assessment of the treatment, carried out as described above, of the hair tresses with formulation 1c according to the invention, comparative formulation C2c and control formulation 0c (placebo without test substance).

TABLE 5

Results of the conditioning of hair from shampoo formulation

|  | Wet comb-ability | Wet feel | Dry comb-ability | Dry feel | Shine |
|---|---|---|---|---|---|
| Formulation 1c according to the invention | 3.7 | 3.7 | 3.5 | 4.3 | 4.2 |
| Comparative formulation C2c (not according to the invention) | 3.2 | 3.1 | 3.1 | 3.8 | 3.3 |
| Control formulation 0c (placebo) | 2.4 | 2.4 | 2.6 | 3.2 | 2.5 |

The results surprisingly show that formulation 1c according to the invention with microemulsion ME18 according to the invention is given significantly better evaluations that comparative formulation C2c with comparative example 3 according to the prior art. The good evaluation of the shine properties of all formulations according to the invention is emphasized particularly clearly.

TABLE 6

Results of the conditioning of hair from hair rinse formulations

|  | Wet comb-ability | Wet feel | Dry comb-ability | Dry feel | Shine |
|---|---|---|---|---|---|
| Formulation 1d according to the invention | 4.9 | 5.0 | 4.8 | 4.8 | 4.4 |
| Comparative formulation C2d (not according to the invention) | 4.3 | 4.4 | 4.5 | 4.5 | 3.9 |
| Control formulation 0d | 3.8 | 3.9 | 3.9 | 3.8 | 2.9 |

Also in the hair rinse application, formulation 1d according to the invention with microemulsion ME18 according to the invention exhibits very good cosmetic evaluations in the sensory assessment. Here, the already very good properties of comparative formulation C2d with comparative example 3 were yet further increased by formulation 1d according to the invention with the microemulsion according to the invention.

A significantly better evaluation is also achieved in the case of shine through use of formulation 1d according to the invention.

3.) Testing the Frictional Values on Dry Hair by Means of Friction Test:

The conditioning effect of the products on dry hair was investigated with the help of a frictional force measurement method (see also US 2009/0324530). For this, an instrument from Instron (Instron 5942, Instron Deutschland GmbH, Pfungstadt, Germany) was used.

The instrument measures the force which is necessary to pull a slide over a real hair tress. The difference in the force from the measurement before and the measurement after the treatment with the conditioning agent gives the frictional value reduction, and thus an objectively ascertained value for the quality of the conditioner used. The slide weighed 200 g and measured 6×7 cm×0.5 cm and was equipped with a solid rubber surface. For each hair tress, this surface was renewed. Real hair tresses predamaged by bleaching and prewashed (7 cm in width, 18 cm free hair length, ca. 8.5 g) were used.

Treatment of the Hair Tresses:

The products were applied from a hair rinse. The microemulsion according to the invention was investigated in comparison to comparative examples 2 and 4. The corresponding formulations are summarized in Table 7.

TABLE 7

Hair rinse formulations for testing the friction on hair.

| Formulation examples | 0e | C1e | 2e | C3e |
|---|---|---|---|---|
| TEGO ® Alkanol 16, Evonik Goldschmidt GmbH (INCI: Cetyl Alcohol)) | 5.00% | 5.00% | 5.00% | 5.00% |
| TEGINACID ® C, Evonik Goldschmidt GmbH (INCI: Ceteareth-25) | 0.50% | 0.50% | 0.50% | 0.50% |
| VARISOFT ® 300, 30% strength, Evonik Goldschmidt GmbH (INCI: Cetrimonium Chloride) | 3.30% | 3.30% | 3.30% | 3.30% |
| Comparative Example 4 |  | 2.27% |  |  |
| Microemulsion ME18 (according to the invention) |  |  | 1.67% |  |
| Comparative Example 2 |  |  |  | 0.59% |
| Water | 90.75% | 88.45% | 89.05% | 90.15% |
| Neolone PE | 0.45% | 0.45% | 0.45% | 0.45% |

The hair rinse formulations were applied to the hair tress in a concentration of 0.5 g/2 g of hair, distributed evenly over the course of 1 min and worked in, left to react for 1 min and rinsed out with 38° C. warm water for 3 min. The hair tresses were left to dry overnight at 22° C. and 50% relative atmospheric humidity before being measured on the Instron force measuring device by means of the method described above.

The resulting frictional value reductions as a result of using the conditioners are shown in FIG. 1.

It is evident from the measurement values that a significant reduction in friction can be achieved with comparison formulations C1e and C3e with comparative examples 4 and 2 and formulation 2e according to the invention with microemulsion 1 according to the invention.

It is also evident that a more pronounced reduction in friction can be achieved with formulation 2e according to the invention with microemulsion ME18 according to the invention than with comparison formulation C1e with comparative example 4 according to the prior art. Consequently, non-inventive comparative example 4 (microemulsion according to the prior art) is less effective than formulation 2e according to the invention with microemulsion ME18 according to the invention.

Formulation C3e with comparative example 2 contains the same quaternary siloxane structure as formulation 2e according to the invention with microemulsion ME18 according to the invention. Surprisingly, a significantly more marked reduction in friction was found with formulation 2e. Consequently, microemulsion ME18 represents a clear improvement of the prior art.

Further Formulation Examples

The formulation examples given in the tables below show exemplary representatives of a multitude of possible compositions according to the invention.

If the preparation of the formulation requires the separate preparation and/or mixing of formulation constituents beforehand, this is referred to as a multiphase preparation.

If a two-phase preparation is required, the two phases are labelled A and B in the stated tables. In the case of three-phase processes, the three phases are called A, B and C. Unless stated otherwise, the data in the tables below is data in % by weight.

| Formulation Example 1) Clear Shampoo | |
|---|---|
| TEXAPON ® NSO, Cognis, 28% strength (INCI: Sodium Laureth Sulfate) | 32.00% |
| Microemulsion ME7 | 2.50% |
| Perfume | 0.50% |
| Water | 55.50% |
| TEGO ® Betain F 50, Evonik Goldschmidt GmbH, 38% strength (INCI: Cocamidopropyl Betaine) | 8.00% |
| ANTIL ® 171 Evonik Goldschmidt GmbH (INCI: PEG-18 Glyceryl Oleate/Cocoate) | 1.00% |
| NaCl | 0.50% |
| Preservative | q.s. |

| Formulation Example 2) Shampoo, PEG- & sulphate free | |
|---|---|
| REWOTERIC ® AM C, Evonik Goldschmidt GmbH, 32% strength, (INCI: Sodium Cocoamphoacetate) | 15.00% |
| Plantapon ACG 50, Cognis (INCI: Disodium Cocoyl Glutamate) | 3.80% |
| Microemulsion ME9 | 2.00% |
| Perfume | 0.30% |
| Water | 64.30% |
| TEGO ® Betain F 50, Evonik Goldschmidt GmbH, 38% strength, (INCI: Cocamidopropyl Betaine) | 10.00% |
| VARISOFT ® PATC, Evonik Goldschmidt GmbH, (INCI: Palmitamidopropyltrimonium Chloride) | 2.30% |
| ANTIL ® SPA 80, Evonik Goldschmidt GmbH, (INCI: Isostearamide MIPA, Glyceryl Laurate) | 2.00% |
| Preservative | 0.30% |
| Citric Acid, 30% strength | q.s. |

| Formulation Example 3) Clear Conditioning Shampoo | |
|---|---|
| TEXAPON ® NSO, Cognis, 28% strength (INCI: Sodium Laureth Sulfate) | 32.00% |
| ANTIL ® 200, Evonik Goldschmidt GmbH (INCI: PEG-200 Hydrogenated Glyceryl Palmate; PEG-7 Glyceryl Cocoate) | 2.00% |
| Microemulsion ME18 | 2.00% |
| Perfume | 0.25% |
| Water | 55.25% |
| Polymer JR 400, Amerchol (INCI: Polyquaternium-10) | 0.20% |
| TEGO ® Betain F 50, Evonik Goldschmidt GmbH, 38% strength (INCI: Cocamidopropyl Betaine) | 8.00% |
| NaCl | 0.30% |
| Preservative | q.s. |

| Formulation Example 4) Clear Conditioning Shampoo | |
|---|---|
| TEXAPON ® NSO, Cognis, 28% strength (INCI: Sodium Laureth Sulfate) | 32.00% |
| ANTIL ® 200, Evonik Goldschmidt GmbH (INCI: PEG-200 Hydrogenated Glyceryl Palmate; PEG-7 Glyceryl Cocoate) | 2.00% |
| ABIL ® Quat 3272, Evonik Goldschmidt GmbH (INCI: Quaternium-80) | 0.75% |
| Microemulsion ME12 | 1.50% |
| Perfume | 0.25% |
| Water | 55.00% |
| Polymer JR 400, Amerchol (INCI: Polyquaternium-10) | 0.20% |
| TEGO ® Betain F 50, Evonik Goldschmidt GmbH, 38% strength (INCI: Cocamidopropyl Betaine) | 8.00% |
| NaCl | 0.30% |
| Preservative | q.s. |

| Formulation Example 5) Clear Conditioning Shampoo | |
|---|---|
| TEXAPON ® NSO, Cognis, 28% strength (INCI: Sodium Laureth Sulfate) | 32.00% |
| ANTIL ® 200, Evonik Goldschmidt GmbH (INCI: PEG-200 Hydrogenated Glyceryl Palmate; PEG-7 Glyceryl Cocoate) | 2.00% |
| ABIL ® B 8832, Evonik Goldschmidt GmbH (INCI: Bis-PEG/PPG-20/20 Dimethicone) | 0.50% |
| Microemulsion ME18 | 3.50% |
| Perfume | 0.25% |
| Water | 53.25% |
| Polymer JR 400, Amerchol (INCI: Polyquaternium-10) | 0.20% |
| TEGO ® Betain F 50, Evonik Goldschmidt GmbH, 38% strength (INCI: Cocamidopropyl Betaine) | 8.00% |
| NaCl | 0.30% |
| Preservative | q.s. |

| Formulation Example 6) Clear Conditioning Shampoo | |
|---|---|
| TEXAPON ® NSO, Cognis, 28% strength (INCI: Sodium Laureth Sulfate) | 32.00% |
| VARISOFT ® PATC, Evonik Goldschmidt GmbH (INCI: Palmitamidopropyltrimonium Chloride) | 1.50% |
| REWODERM ® LI S 80, Evonik Goldschmidt GmbH (INCI: PEG-200 Hydrogenated Glyceryl Palmate; PEG-7 Glyceryl Cocoate) | 2.00% |
| Microemulsion ME28 | 2.50% |
| Perfume | 0.25% |
| Water | 52.05% |
| TEGO ® Cosmo C 100, Evonik Goldschmidt GmbH, (INCI: Creatine) | 1.00% |
| Jaguar C-162, Rhodia (INCI: Hydroxypropyl Guar Hydroxypropyltrimonium Chloride) | 0.20% |
| TEGO ® Betain F 50, Evonik Goldschmidt GmbH, 38% strength (INCI: Cocamidopropyl Betaine) | 8.00% |
| NaCl | 0.50% |
| Preservative | q.s. |

| Formulation Example 7) Clear Conditioning Shampoo | |
|---|---|
| TEXAPON ® NSO, Cognis, 28% strength (INCI: Sodium Laureth Sulfate) | 32.00% |
| REWODERM ® LI S 80, Evonik Goldschmidt GmbH (INCI: PEG-200 Hydrogenated Glyceryl Palmate; PEG-7 Glyceryl Cocoate) | 2.00% |
| Microemulsion ME18 | 2.50% |
| Perfume | 0.25% |
| Water | 53.55% |
| TEGO ® Cosmo C 100, Evonik Goldschmidt GmbH, (INCI: Creatine) | 1.00% |
| Jaguar C-162, Rhodia (INCI: Hydroxypropyl Guar Hydroxypropyltrimonium Chloride) | 0.20% |
| TEGO ® Betain F 50, Evonik Goldschmidt GmbH, 38% strength (INCI: Cocamidopropyl Betaine) | 8.00% |
| NaCl | 0.50% |
| Preservative | q.s. |

| Formulation Example 8) Pearlized Shampoo | |
|---|---|
| TEXAPON ® NSO, Cognis, 28% strength (INCI: Sodium Laureth Sulfate) | 32.00% |
| Microemulsion ME6 | 5.50% |
| Perfume | 0.25% |
| Water | 49.25% |

| Formulation Example 8) Pearlized Shampoo | |
| --- | --- |
| TEGO ® Betain F 50, Evonik Goldschmidt GmbH, 38% strength (INCI: Cocamidopropyl Betaine) | 8.00% |
| TEGO ® Pearl N 300 Evonik Goldschmidt GmbH (INCI: Glycol Distearate; Laureth-4; Cocamidopropyl Betaine) | 2.00% |
| ANTIL ® 171 Evonik Goldschmidt GmbH (INCI: PEG-18 Glyceryl Oleate/Cocoate) | 2.50% |
| NaCl | 0.50% |
| Preservative | q.s. |

| Formulation Example 9) Shampoo, PEG- & sulfate free | | |
| --- | --- | --- |
| A | REWOTERIC ® AMC, Evonik Goldschmidt GmbH, 32% strength, (INCI: Sodium Cocoamphoacetate) | 20.00% |
| | REWOPOL ® SB F 12 P, Evonik Goldschmidt, 96% strength, (INCI: Disodium Lauryl Sulphosuccinate) | 5.90% |
| | Microemulsion ME18 | 2.00% |
| | ANTIL ® SPA 80, Evonik Goldschmidt GmbH, (INCI: Isostearamide MIPA, Glyceryl Laurate) | 1.70% |
| B | Water | 63.20% |
| | Citric Acid, 30% strength | 3.60% |
| C | ANTIL ® HS 60, Evonik Goldschmidt GmbH, (INCI: Cocamidopropyl Betaine; Glyceryl Laurate) | 3.00% |
| | Preservative | 0.60% |

| Formulation Example 10) Rinse-Off Conditioner | |
| --- | --- |
| Water | 85.50% |
| VARISOFT ® BT 85, Evonik Goldschmidt GmbH (INCI: Behentrimonium Chloride) | 3.00% |
| Microemulsion ME9 | 5.50% |
| TEGO ® Alkanol 1618, Evonik Goldschmidt GmbH (INCI: Cetearyl Alcohol) | 5.00% |
| Preservative, Perfume | q.s. |

| Formulation Example 11) Rinse-Off Conditioner | |
| --- | --- |
| Water | 90.20% |
| VARISOFT ® EQ 65, Evonik Goldschmidt GmbH (INCI: Distearyl Dimonium Chloride, Cetearyl Alcohol) | 2.00% |
| VARISOFT ® BT 85, Evonik Goldschmidt GmbH (INCI: Behentrimonium Chloride) | 1.00% |
| Microemulsion ME18 | 1.80% |
| TEGO ® Alkanol 1618, Evonik Goldschmidt GmbH (INCI: Cetearyl Alcohol) | 5.00% |
| Preservative, Perfume | q.s. |

| Formulation Example 12) Rinse-Off Conditioner | |
| --- | --- |
| Water | 87.20% |
| VARISOFT ® EQ 65, Evonik Goldschmidt GmbH (INCI: Distearyl Dimonium Chloride, Cetearyl Alcohol) | 2.00% |
| VARISOFT ® BT 85, Evonik Goldschmidt GmbH (INCI: Behentrimonium Chloride) | 2.00% |
| ABIL ® Quat 3272, Evonik Goldschmidt GmbH (INCI: Quaternium-80) | 0.50% |
| Microemulsion ME18 | 3.30% |
| TEGO ® Alkanol 1618, Evonik Goldschmidt GmbH (INCI: Cetearyl Alcohol) | 5.00% |
| Preservative, Perfume | q.s. |

| Formulation Example 13) Rinse-Off Conditioner | |
| --- | --- |
| TEGINACID ® C, Evonik Goldschmidt GmbH (INCI: Ceteareth-25) | 0.50% |
| TEGO ® Alkanol 16, Evonik Goldschmidt GmbH (INCI: Cetyl Alcohol) | 2.00% |
| TEGO ® Amid S 18, Evonik Goldschmidt GmbH (INCI: Stearamidopropyl Dimethylamine) | 1.00% |
| Microemulsion ME28 | 5.50% |
| Propylene Glycol | 2.00% |
| Citric Acid Monohydrate | 0.30% |
| Water | 88.70% |
| Preservative, Perfume | q.s. |

| Formulation Example 14) Rinse-Off Conditioner | |
| --- | --- |
| TEGINACID ® C, Evonik Goldschmidt GmbH (INCI: Ceteareth-25) | 0.50% |
| TEGO ® Alkanol 16, Evonik Goldschmidt GmbH (INCI: Cetyl Alcohol) | 5.00% |
| TEGOSOFT ® DEC, Evonik Goldschmidt GmbH (INCI: Diethylhexyl Carbonate) | 1.00% |
| Microemulsion ME18 | 3.50% |
| Water | 87.20% |
| TEGO ® Cosmo C 100 Evonik Goldschmidt GmbH (INCI: Creatine) | 0.50% |
| Propylene Glycol | 2.00% |
| Citric Acid Monohydrate | 0.30% |
| Preservative, Perfume | q.s. |

| Formulation Example 15) Leave-In Conditioner Spray | |
| --- | --- |
| Lactic Acid, 80% | 0.40% |
| Water | 92.30% |
| TEGO ® Amid S 18, Evonik Goldschmidt GmbH (INCI: Stearamidopropyl Dimethylamine) | 1.20% |
| TEGIN ® G 1100 Pellets, Evonik Goldschmidt GmbH (INCI: Glycol Distearate) | 0.60% |
| TEGO ® Care PS, Evonik Goldschmidt GmbH (INCI: Methyl Glucose Sesquistearate) | 1.20% |
| TEGOSOFT ® DEC, Evonik Goldschmidt GmbH (INCI: Diethylhexyl Carbonate) | 0.30% |
| Microemulsion ME6 | 4.00% |
| Preservative, Perfume | q.s. |

| Formulation Example 16) Leave-In Conditioner Spray | |
| --- | --- |
| TAGAT ® CH-40, Evonik Goldschmidt GmbH (INCI: PEG-40 Hydrogenated Castor Oil) | 2.00% |
| Ceramide VI, Evonik Goldschmidt GmbH (INCI: Ceramide 6 II) | 0.05% |
| Perfume | 0.20% |
| Water | 81.95% |
| Microemulsion ME6 | 9.50% |
| LACTIL ® Evonik Goldschmidt GmbH (INCI: Sodium Lactate; Sodium PCA; Glycine; Fructose; Urea; Niacinamide; Inositol; Sodium benzoate; Lactic Acid) | 2.00% |
| TEGO ® Betain F 50 Evonik Goldschmidt GmbH 38% (INCI: Cocamidopropyl Betaine) | 2.30% |
| Citric Acid (10% in water) | 2.00% |

| Formulation Example 17) Leave-In Conditioner Foam | |
| --- | --- |
| Microemulsion ME18 | 3.50% |
| TAGAT ® CH-40, Evonik Goldschmidt GmbH (INCI: PEG-40 Hydrogenated Castor Oil) | 0.50% |

Formulation Example 17) Leave-In Conditioner Foam

| | |
|---|---|
| Perfume | 0.30% |
| TEGO ® Betain 810, Evonik Goldschmidt GmbH (INCI: Capryl/Capramidopropyl Betaine) | 2.00% |
| Water | 91.00% |
| TEGO ® Cosmo C 100, Evonik Goldschmidt GmbH (INCI: Creatine) | 0.50% |
| TEGOCEL ® HPM 50, Evonik Goldschmidt GmbH (INCI: Hydroxypropyl Methylcellulose) | 0.30% |
| VARISOFT ® 300, Evonik Goldschmidt GmbH (INCI: Cetrimonium Chloride) | 1.30% |
| LACTIL ® Evonik Goldschmidt GmbH (INCI: Sodium Lactate; Sodium PCA; Glycine; Fructose; Urea; Niacinamide; Inositol; Sodium benzoate; Lactic Acid) | 0.50% |
| Citric Acid (30% in water) | 0.10% |
| Preservative | q.s. |

Formulation Example 18) Strong Hold Styling Gel

| | |
|---|---|
| TEGO ® Carbomer 141, Evonik Goldschmidt GmbH (INCI: Carbomer) | 1.20% |
| Water | 65.00% |
| NaOH, 25% | 2.70% |
| PVP/VA W-735, ISP (INCI: PVP/VA Copolymer) | 16.00% |
| Microemulsion ME18 | 2.50% |
| Alcohol Denat. | 10.00% |
| TAGAT ® O 2 V, Evonik Goldschmidt GmbH (INCI: PEG-20 Glyceryl Oleate) | 2.00% |
| Perfume | 0.30% |
| ABIL ® B 88183, Evonik Goldschmidt GmbH (INCI: PEG/PPG-20/6 Dimethicone) | 0.30% |
| Preservative | q.s. |

Formulation Example 19) Foaming body care composition

| | |
|---|---|
| TEXAPON ® NSO, Cognis, 28% strength (INCI: Sodium Laureth Sulfate) | 14.30% |
| Perfume | 0.30% |
| Microemulsion ME18 | 1.50% |
| REWOTERIC ® AM C, Evonik Goldschmidt GmbH, 32% strength (INCI: Sodium Cocoamphoacetate) | 8.00% |
| Water | 73.90% |
| TEGOCEL ® HPM 50, Evonik Goldschmidt GmbH (INCI: Hydroxypropyl Methylcellulose) | 0.50% |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 1.00% |
| Citric Acid Monohydrate | 0.50% |

Formulation Example 20) Body care composition

| | |
|---|---|
| TEXAPON ® NSO, Cognis, 28% strength (INCI: Sodium Laureth Sulfate) | 30.00% |
| TEGOSOFT ® PC 31, Evonik Goldschmidt GmbH (INCI: Polyglyceryl-3 Caprate) | 0.50% |
| Microemulsion ME12 | 1.50% |
| Perfume | 0.30% |
| Water | 52.90% |
| TEGOCEL ® HPM 4000, Evonik Goldschmidt GmbH (INCI: Hydroxypropyl Methylcellulose) | 0.30% |
| REWOTERIC ® AM C, Evonik Goldschmidt GmbH, 32% strength (INCI: Sodium Cocoamphoacetate) | 10.00% |
| Citric Acid Monohydrate | 0.50% |
| REWODERM ® LI S 80, Evonik Goldschmidt GmbH (INCI: PEG-200 Hydrogenated Glyceryl Palmate; PEG-7 Glyceryl Cocoate) | 2.00% |
| TEGO ® Pearl N 300, Evonik Goldschmidt GmbH (INCI: Glycol Distearate; Laureth-4; Cocamidopropyl Betaine) | 2.00% |

Formulation Example 21) Foaming body care composition

| | |
|---|---|
| TEXAPON ® NSO, Cognis, 28% strength (INCI: Sodium Laureth Sulfate) | 14.30% |
| Perfume | 0.30% |
| Microemulsion ME18 | 1.00% |
| REWOTERIC ® AM C, Evonik Goldschmidt GmbH, 32% strength (INCI: Sodium Cocoamphoacetate) | 8.00% |
| Water | 75.10% |
| Polyquaternium-7 | 0.30% |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 0.50% |
| Citric Acid Monohydrate | 0.50% |

Formulation Example 22) Mild Foam Bath

| | |
|---|---|
| TEXAPON ® NSO, Cognis, 28% strength (INCI: Sodium Laureth Sulfate) | 27.00% |
| REWOPOL ® SB FA 30, Evonik Goldschmidt GmbH, 40% strength (INCI: Disodium Laureth Sulphosuccinate) | 12.00% |
| TEGOSOFT ® LSE 65 K SOFT, Evonik Goldschmidt GmbH (INCI: Sucrose Cocoate) | 2.00% |
| Water | 38.00% |
| REWOTERIC ® AM C, Evonik Goldschmidt GmbH, 32% strength (INCI: Sodium Cocoamphoacetate) | 13.00% |
| Microemulsion ME7 | 1.50% |
| Citric Acid (30% in water) | 3.00% |
| ANTIL ® 171 Evonik Goldschmidt GmbH (INCI: PEG-18 Glyceryl Oleate/Cocoate) | 1.50% |
| TEGO ® Pearl N 300 Evonik Goldschmidt GmbH (INCI: Glycol Distearate; Laureth-4; Cocamidopropyl Betaine) | 2.00% |

Formulation Example 23) Rinse-Off Conditioner

| | |
|---|---|
| Water | 88.20% |
| VARISOFT ® 300, Evonik Goldschmidt GmbH (INCI: Cetrimonium Chloride) | 2.00% |
| VARISOFT ® BT 85, Evonik Goldschmidt GmbH (INCI: Behentrimonium Chloride) | 2.00% |
| ABIL ® OSW 5, Evonik Goldschmidt GmbH (INCI: Cyclopenta Siloxane; Dimethiconol) | 1.00% |
| Microemulsion ME6 | 1.80% |
| TEGO ® Alkanol 1618, Evonik Goldschmidt GmbH (INCI: Cetearyl Alcohol) | 5.00% |
| Preservative, Perfume | q.s. |

Formulation Example 24) Rinse-Off Conditioner

| | |
|---|---|
| Water | 87.20% |
| VARISOFT ® EQ 65, Evonik Goldschmidt GmbH (INCI: Distearyl Dimonium Chloride, Cetearyl Alcohol) | 2.00% |

Formulation Example 24) Rinse-Off Conditioner

| | |
|---|---|
| VARISOFT ® BT 85, Evonik Goldschmidt GmbH (INCI: Behentrimonium Chloride) | 2.00% |
| ABIL ® Soft AF 100, Evonik Goldschmidt GmbH (INCI: Methoxy PEG/PPG-7/3 Aminopropyl Dimethicone) | 1.00% |
| Microemulsion ME18 | 2.80% |
| TEGO ® Alkanol 1618, Evonik Goldschmidt GmbH (INCI: Cetearyl Alcohol) | 5.00% |
| Preservative, Perfume | q.s. |

Formulation Example 25) Rinse-Off Conditioner

| | |
|---|---|
| Water | 88.20% |
| VARISOFT ® BT 85, Evonik Goldschmidt GmbH (INCI: Behentrimonium Chloride) | 3.00% |
| SF 1708, Momentive (INCI: Amodimethicone) | 2.00% |
| Microemulsion ME18 | 1.80% |
| TEGO ® Alkanol 1618, Evonik Goldschmidt GmbH (INCI: Cetearyl Alcohol) | 5.00% |
| Preservative, Perfume | q.s. |

Formulation Example 26) moisturizing skin cleansing composition

| | | |
|---|---|---|
| A | TEXAPON ® NSO, Cognis, 28% strength, (INCI: Sodium Laureth Sulfate) | 30.00 |
| | Microemulsion ME12 | 1.70 |
| | Perfume | 0.30 |
| B | Water | 54.60 |
| | TEGOCEL ® fluid HPM 4000, Evonik Goldschmidt GmbH, (INCI: Hydroxypropyl Methylcellulose) | 1.20 |
| | TEGO ® Betain C 60, Evonik Goldschmidt GmbH, 46% strength, (INCI: Cocamidopropyl Betaine) | 8.10 |
| | TEGOSOFT ® APM, Evonik Goldschmidt GmbH, (INCI: PPG-3 Myristyl Ether) | 1.00 |
| | Cutina TS, Cognis (INCI: PEG-3 Distearate) | 1.00 |
| | REWODERM ® LI S 80, Evonik Goldschmidt GmbH, (INCI: PEG-200 Hydrogenated Glyceryl Palmate; PEG-7 Glyceryl Cocoate) | 1.50 |
| | Preservative | 0.60 |
| | Citric Acid, 30% strength | q.s. |

Formulation Example 27) shower gel

| | |
|---|---|
| TEXAPON ® NSO, Cognis, 28% strength (INCI: Sodium Laureth Sulfate) | 15.00 |
| Microemulsion ME28 | 1.50 |
| Perfume | 0.30 |
| PGFAC-S, Cognis (INCI: Sodium cocoyl hydrolyzed wheat protein glutamate) | 1.50 |
| REWOPOL SB CS 50 B, Evonik Goldschmidt GmbH, 40% strength, (INCI: Disodium PEG-5 Laurylcitrate Sulphosuccinate; Sodium Laureth Sulfate) | 7.50 |
| Water | 58.10 |
| TEGO ® Betain F 50, Evonik Goldschmidt GmbH, 38% strength, (INCI: Cocamidopropyl Betaine) | 9.00 |
| TEGO ® Betain 810, Evonik Goldschmidt GmbH, 38% strength, (INCI: Capryl/Capramidopropyl Betaine) | 4.00 |
| Polyquaternium-7, Nalco, (INCI: Merquat 550) | 0.50 |
| ANTIL ® 200, Evonik Goldschmidt GmbH, (INCI: PEG-200 Hydrogenated Glyceryl Palmate; PEG-7 Glyceryl Cocoate) | 2.30 |
| Preservative | 0.30 |

Formulation Example 28) body cleansing composition

| | | |
|---|---|---|
| A | TEXAPON ® NSO Cognis 28% strength, (INCI: Sodium Laureth Sulfate) | 30.00 |
| | Microemulsion ME18 | 1.50 |
| | ABIL ® B 8832, Evonik Goldschmidt GmbH, (INCI: Bis-PEG/PPG-20/20 Dimethicone) | 0.30 |
| | Perfume | 0.30 |
| B | Water | 51.00 |
| | TEGOCEL ® fluid HPM 4000, Evonik Goldschmidt GmbH, (INCI: Hydroxypropyl Methylcellulose) | 1.20 |
| | Citric Acid Monohydrate | 0.50 |
| | REWOTERIC ® AM C, Evonik Goldschmidt GmbH, 32% strength, (INCI: Sodium Cocoamphoacetate) | 10.00 |
| | Cutina TS, Cognis (INCI: PEG-3 Distearate) | 2.00 |
| | REWODERM ® LI S 80, Evonik Goldschmidt GmbH, (INCI: PEG-200 Hydrogenated Glyceryl Palmate; PEG-7 Glyceryl Cocoate) | 2.60 |
| | Preservative | 0.60 |
| | Citric Acid, 30% strength | q.s. |

Formulation Example 29) body cleansing foam

| | |
|---|---|
| TEXAPON ® NSO, Cognis, 28% strength (INCI: Sodium Laureth Sulfate) | 14 |
| Perfume | 0.3 |
| Microemulsion ME18 | 0.7 |
| REWOTERIC ® AM C, Evonik Goldschmidt GmbH, 32% strength (INCI: Sodium Cocoamphoacetate) | 8 |
| Water | 74.8 |
| TEGOCEL ® HPM 50, Evonik Goldschmidt GmbH (INCI: Hydroxypropyl Methylcellulose) | 0.5 |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 1 |
| Panthenol, BASF, (INCI: D-Panthenol USP) | 0.2 |
| Citric Acid Monohydrate | 0.5 |

Formulation Example 30) Turbid Conditioning Shampoo

| | |
|---|---|
| TEXAPON ® NSO, Cognis, 28% strength (INCI: Sodium Laureth Sulfate) | 32.00 |
| ANTIL ® 200, Evonik Goldschmidt GmbH (INCI: PEG-200 Hydrogenated Glyceryl Palmate; PEG-7 Glyceryl Cocoate) | 2.00 |
| Microemulsion ME12 | 1.00 |
| Perfume | 0.25 |
| Water | 53.25 |
| Polymer JR 400, Amerchol (INCI: Polyquaternium-10) | 0.20 |
| TEGO ® Betain F 50, Evonik Goldschmidt GmbH, 38% strength (INCI: Cocamidopropyl Betaine) | 8.00 |
| DC1503 Fluid, Dow Corning, (INCI: Dimethicone, Dimethiconol) | 1.00 |
| TEGO ® Pearl N 300 Evonik Goldschmidt GmbH (INCI: Glycol Distearate; Laureth-4; Cocamidopropyl Betaine) | 2.00 |
| NaCl | 0.30 |
| Preservative | q.s. |

Formulation Example 31) Mild Hair & Body Wash, PEG- and Sulfate-free

| | |
|---|---|
| Plantacare ® 1200 UP, Cognis, 50% strength, (INCI: Lauryl Glucoside) | 11.40% |
| Plantacare ® 818 UP, Cognis, 51% strength, (INCI: Coco Glucoside) | 5.60% |
| Water | 61.60% |
| ANTIL ® SOFT SC, Evonik Goldschmidt GmbH, (INCI: Sorbitan Sesquicaprylate) | 0.90% |
| Microemulsion ME28 | 1.00% |
| TEGOSOFT ® LSE 65 K SOFT, Evonik Goldschmidt GmbH, (INCI: Sucrose Cocoate) | 1.50% |
| TEGO ® Betain F 50, Evonik Goldschmidt GmbH, 38% strength, (INCI: Cocamidopropyl Betaine) | 18.00% |

-continued

| Formulation Example 31) Mild Hair & Body Wash, PEG- and Sulfate-free | |
|---|---|
| Perfume, preservative | q.s. |
| Citric Acid, 30% | q.s. |

| Formulation Example 32) Sprayable Hair milk, PEG-free | | |
|---|---|---|
| A | Water | 95.30% |
| | Lactic Acid, 80% strength | 0.40 |
| B | TEGO ® AMID S 18, Evonik Goldschmidt GmbH, (INCI: Stearamidopropyl Dimethylamine) | 1.20% |
| | TEGIN ® G 1100 Pellets, Evonik Goldschmidt GmbH, (INCI: Glycol Distearate) | 0.60% |
| | TEGO ® Care PS, Evonik Goldschmidt GmbH, (INCI: Methyl Glucose Sesquistearate) | 1.20% |
| | TEGOSOFT ® DEC, Evonik Goldschmidt GmbH, (INCI: Diethylhexyl Carbonate) | 0.30% |
| | Microemulsion ME18 | 1.00% |
| | Perfume, preservative | q.s. |

Textile Care Application Technology

To determine the softening effect of the microemulsion according to the invention on textile fabrics, cotton towels were treated therewith.

Preparation of a Siloxane Macroemulsion (not According to the Invention—Comparative Example)

Formulation Example T1

20 parts of siloxane 5 heated to 40° C. to 80° C. are placed in a beaker with propeller stirrer with stirring. Then, 10 parts by weight of dipropylene glycol, 10 parts by weight of a fatty alcohol ethoxylate with a degree of ethoxylation of 6 were added in order with stirring. Finally, the mixture is made up to 100 parts by weight with water and stirred until the mixture has cooled to room temperature, but at least for 15 min.

Preparation of a Siloxane Microemulsion (According to the Invention) of Formulation Example T2

Corresponds to formulation example microemulsion ME 33

Preparation of Fabric Softener Formulations:

Formulation Example T3

Ca. 5% by Weight of Siloxane-Free Fabric Softener Formulation (not According to the Invention—Reference)

33.3 g of a liquid REWOQUAT® WE 18 heated to 40 to 80° C. (trade name of Evonik Goldschmidt GmbH, triethanolamine-based esterquat with an active content of 90%) were added to 556 g of tap water heated to 45-65° C. with stirring, and the mixture was stirred for 20 min using a propeller stirrer at 45-65° C. and cooled to room temperature over the course of ca. one hour.

Formulation Example T4

Siloxane-Containing Fabric Softener Formulation (not According to the Invention—Comparative Example)

33.3 g of a liquid REWOQUAT® WE 18, heated to 40 to 80° C., were weighed into a 50 ml centrifuge tube made of polypropylene together with 0.28 g of siloxane 5 and intensively mixed using a vortex mixer by shaking. This cloudy mixture was added in its entirety, with stirring, to 556 g of tap water heated to 45-65° C., and the mixture was stirred for 20 min using a propeller stirrer at 45-65° C. and cooled to room temperature over the course of ca. one hour.

Formulation Example T5

Siloxane-Containing Fabric Softener Formulation (not According to the Invention—Comparative Example)

33.3 g of a liquid REWOQUAT® WE 18 heated to 40 to 80° C. (trade name of Evonik Goldschmidt GmbH, triethanolamine-based esterquat with an active content of 90%) were added, with stirring, to 556 g of tap water heated to 45-65° C., and the mixture was stirred for 20 min using a propeller stirrer at 45-65° C., and then 1.40 g of the siloxane macroemulsion from formulation example T2 were added and the mixture was cooled to room temperature over the course of ca. one hour.

Formulation Example T6

Siloxane-Containing Fabric Softener Formulation (According to the Invention)

33.3 g of a liquid REWOQUAT® WE 18 heated to 40 to 80° C. (trade name of Evonik Goldschmidt GmbH, triethanolamine-based esterquat with an active content of 90%) were added, with stirring, to 556 g of tap water heated to 45-65° C., the mixture was stirred for 20 min using a propeller stirrer at 45-65° C., and then 1.37 g of the siloxane microemulsion from formulation example T3 were added and the mixture was cooled to room temperature over the course of ca. one hour.

Pretreatment of the Cotton Fabric:

Cotton terry fabric measuring 80 cm×50 cm with a weight per area of ca. 350 g/m$^2$ was washed twice using universal detergent powder, rinsed twice, spun and hung on a line as one layer to dry in the air.

Treatment of Cotton Fabric:

The above-described formulations T3 to T6 were diluted with cold tap water to give rinse solutions whose total active concentration, i.e. the sum of REWOQUAT® WE 18 and Siloxane 5, is 0.025% by weight.

The cotton towels were immersed for 10 min in two liters of the rinse solution. Here, it should be ensured that the towels are wetted uniformly by the rinse solution. The towels were then spun and hung on a line as one layer to dry. The treated cotton terry towels were cut into 10 equal sections measuring 16 cm by 25 cm.

To assess the soft feel, an experienced team of 9 test subjects was assembled which evaluated the anonymized feel samples of the cotton fabric treated with the rinse solutions using a hand panel test. For this, each test subject was given his own cotton towel. The assessment was made on a scale from 0 (hard and unpleasant in feel) to 5 (soft and pleasant in feel) with the option of whole-numbered interim values. To assess the soft feel, the individual evaluations are summed, thus giving a maximum soft feel of 45 for 9 test subjects.

Additionally, a non-obviously marked untreated sample (blank value) was always added among the feel samples.

Summary of the Soft Feel Results

| Formulation Example | Note | Soft feel |
|---|---|---|
| T3 | Without Siloxane 5 | 33 |
| T4 | Siloxane 5 mixed with REWOQUAT ® WE 18 | 29 |
| T5 | Macroemulsion of Siloxane 5 | 32 |
| T6 | Microemulsion of Siloxane 5 | 39 |
| Blank value | Without Siloxane & without REWOQUAT ® WE 18 | 0 |

The data in the table clearly shows that the softness of the cotton fabric can be considerably improved when using a microemulsion of Siloxane 5. By contrast, the direct mixing of REWOQUAT® WE 18 and Siloxane 5, and also the use of a macroemulsion lead to a reduction in the soft feel.

Coatings Application Technology:

| Formulation Example 1) 1C PUR coating | |
|---|---|
| Bayderm Finish 91 UD | 54.0% |
| Water | 45.0% |
| TEGO ® Viskoplus 3030 | 1.0% |

Production of Coatings:

100 grams of 10 PUR coating together with either 0.0, 1.5 or 3.0 grams of microemulsion ME35 or ME36 were weighed into a 180 ml polyethylene beaker (Ø 6 cm) and then homogenized using a Dispermat with a toothed disc (Ø 3 cm) by stirring for 3 minutes at 2000 rpm (sample 1-5). After a standing time of 24 hours, the coating is applied to black, matted PVC film (System Leneta®, 43×28 cm) using a 60 μm box-type applicator. The coating is then dried for 72 hours at room temperature. Alternatively, the coating is applied to beige cowhide leather using a 75 μm wire doctor and likewise dried.

Testing (Stick-) Slip Friction (Coefficient of Sliding Friction):

The coefficients of sliding friction were measured on PVC film using an Instron 3300 instrument (Instron Deutschland GmbH, Pfungstadt, Germany). The instrument measures the force which is required in order to pull a slide over the coated film. The cylindrical slide with a weight of 500 grams and a contact area of 12.6 cm² was equipped here with a felt surface, this surface being renewed for each measurement. The slide is then pulled (with increasing force) until it moves at a speed of 6 mm/s. The tensile force (load) is thus measured which is necessary in order to move the slide. A high stick-slip friction or stick-slip behaviour is evident from considerable fluctuations in the tensile force (load) in the measurement.

Figure 2:
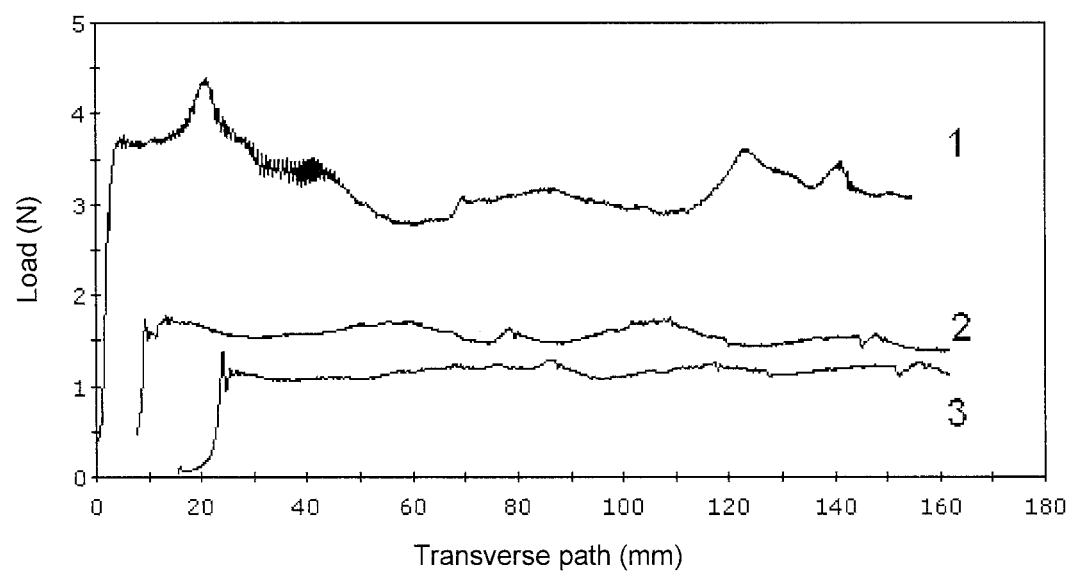
FIG. 2 is part of the examples and shows measurements that the sliding friction decreases as the concentration of the microemulsion increases.

FIG. 2 shows some representative measurement curves. The sliding friction decreases as the concentration of the microemulsion increases. The considerable fluctuations in the load in the case of the non-additized sample point to a large stick-slip friction. By adding ME 35, the fluctuations in the load in the measurement are reduced, i.e. the stick-slip friction becomes less.

Testing Feel:

To assess the haptics, an experienced test subject qualitatively evaluated the coatings applied to cowhide leather. Test subject described sample 1 as rubber-like. By contrast, samples 2 to 5 are perceived as velvety.

Summary of the Testing

| Sample | ME35/gram | ME36/gram | Coefficient of sliding friction cN | Feel |
|---|---|---|---|---|
| 1 | 0.0 | 0.0 | 306 | Rubber |
| 2 | 1.5 | 0.0 | 154 | Velvety |
| 3 | 3.0 | 0.0 | 126 | Velvety |
| 4 | 0.0 | 1.5 | 105 | Velvety |
| 5 | 0.0 | 3.0 | 92 | Velvety |

The invention claimed is:

1. A microemulsion comprising, as a component substantially forming an oil phase, A) a polysiloxane containing at least one quaternary ammonium group and of formula (I)

$$M_a M'_{a1} M''_{a2} M'''_{a3} D_b D'_{b1} D''_{b2} D'''_{b3} T_c T'_{c1} Q_d \qquad \text{formula (I)},$$

where
$M = (R^1{}_3 SiO_{1/2})$
$M' = (R^2 R^1{}_2 SiO_{1/2})$
$M'' = (R^3 R^1{}_2 SiO_{1/2})$
$M''' = (R^4 R^1{}_2 SiO_{1/2})$
$D = (R^1{}_2 SiO_{2/2})$
$D' = (R^2 R^1 SiO_{2/2})$
$D'' = (R^3 R^1 SiO_{2/2})$
$D''' = (R^4 R^1 SiO_{2/2})$
$T = (R^5 SiO_{3/2})$
$T' = (R^2 SiO_{3/2})$
$Q = (SiO_{4/2})$
a=0 to 32;
a1=0 to 10;
a2=0 to 32;
a3=0 to 10;
with the proviso that
a+a1+a2+a3≥3;
b=1 to 600;
b1=0 to 10;
b2=0 to 80;
b3=0 to 20;
c=0 to 30;
c1=0 to 10;
d=0 to 15;
with the proviso that
a2+b2≥1 and
c+c1+d≥1;
$R^1$=independently of one another identical or different linear or branched hydrocarbon radicals having 1 to 30 carbon atoms;
$R^2$=independently of one another identical or different alkoxy or acyloxy radicals;
$R^3$=independently of one another identical or different organic radicals which carry quaternary ammonium functions;
$R^4$=independently of one another identical or different organic epoxy radicals; and
$R^5$=independently of one another identical or different radicals $R^1$, $R^3$ or $R^4$;

B) a nonionic surfactant,
C) a cosurfactant selected from the group consisting of anionic, cationic and amphoteric surfactants, and
D) water; wherein said component B) is selected from the group consisting of glycerol mono- and diesters and sorbitan mono- and diesters of saturated and unsaturated fatty acids, alkylmono- and oligoglycosides, partial esters based on linear, branched, unsaturated or saturated fatty acids, ricinoleic acid, and 12-hydroxystearic acid and glycerol, polyglycerol, pentaerythritol, dipentaerythritol, sugar alcohols, alkylglucosides, and polyglucosides, mono-, di- and trialkylphosphates and salts thereof citric acid, glyceryl caprylate, polyglycerylcaprylate, polyglycerylcaprate and mixtures thereof.

2. The microemulsion according to claim 1, wherein $R^4$ is identical or different radicals selected from the group consisting of

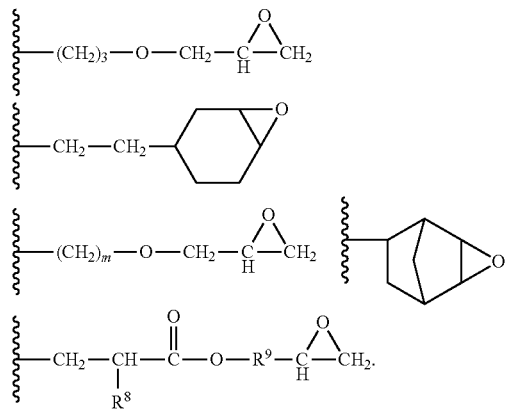

3. The microemulsion according to claim 1, wherein $R^3$ comprises $—R^6—R^7$, wherein
$R^6$ are identical or different divalent radicals selected from the group consisting of

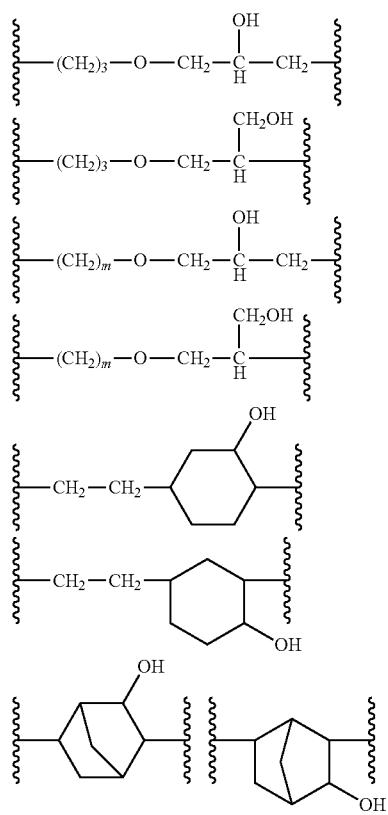

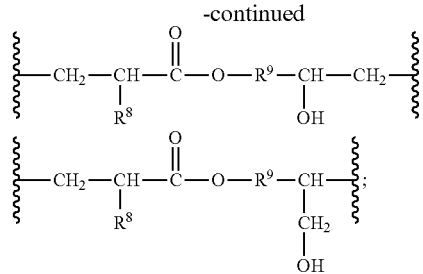

$R^7$ is selected from the group consisting of

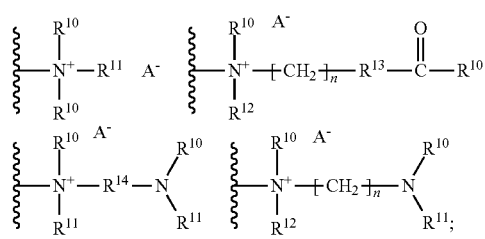

$R^8$ are identical or different radicals selected from the group consisting of hydrogen and an alkyl having 1 to 6 carbon atoms;
$R^9$ are identical or different divalent hydrocarbon radicals;
$R^{10}, R^{11}, R^{12}$ are in each case independently of one another hydrogen alkyl radicals having 1 to 30 carbon atoms or radicals of the formula

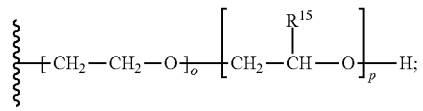

$R^{13}$ are identical or different radicals selected from the group consisting of $—O—$; and $—NR^{16}—$;
$R^{14}$ are identical or different divalent hydrocarbon radicals;
$R^{15}$ are identical or different alkyl, aryl or alkaryl radicals having 1 to 30 carbon atoms;
$R^{16}$ are identical or different radicals selected from the group consisting of hydrogen and an alkyl having 1 to 6 carbon atoms;
m=2 to 18;
n=2 to 18;
o=0 to 30;
p=0 to 30;
$A^-$ are identical or different counterions to positive charges on the quaternized nitrogen groups, and are selected from inorganic or organic anions of acids HA, and derivatives thereof.

4. The microemulsion according to claim 1, wherein c=1 and
c+c1+d=1.

5. The microemulsion according to claim 1, wherein the polysiloxane has an average molecular weight of greater than 4000 g/mol.

6. The microemulsion according to claim 1, wherein said microemulsion is essentially free from alkoxylated compounds.

7. The microemulsion according to claim 1 further comprising a solvent as component E, wherein said solvent is selected from the group consisting of hydrotropes, cyclic carbonates esters of mono- or polycarboxylic acids and polyols.

8. The microemulsion according to claim 7, further comprising at least one of a preservative as component F, and an oil or oil mixture as component G.

9. The microemulsion according to claim 8, wherein
said component A) is present in an amount of from 10% by weight to 60% by weight;
said component B) is present in an amount of from 3% by weight to 30% by weight;
said component C) is present in an amount of from 0% by weight to 30% by weight;
said component D) is present in an amount of from 10% by weight to 75% by weight;
said component E) is present in an amount of from 0% by weight to 35% by weight;
said component F) is present in an amount of from 0% by weight to 1% by weight and
said component G) is present in an amount of from 0% by weight to 50% by weight of the total oil phase consisting of components A) and B),
where the % by weight, apart from in the case of component G), refer to the total microemulsion.

10. A formulation comprising the microemulsion of claim 1.

* * * * *